United States Patent
Neal et al.

(10) Patent No.: US 9,492,178 B2
(45) Date of Patent: Nov. 15, 2016

(54) POROUS SPACERS, INSTRUMENTS, AND METHODS FOR FOOT AND ANKLE FUSION

(71) Applicant: Zimmer, Inc., Warsaw, IN (US)

(72) Inventors: David J. Neal, Morris Plains, NJ (US); Joseph Markham, Hillsborough, NJ (US); Victor Valderrabano, Hofstetten (CH); Richard John Claridge, Scottsdale, AZ (US); John Shirk Kirchner, Birmingham, AL (US); Mehul Dharia, Albuquerque, NM (US); Ray Zubok, Midland Park, NJ (US); Greg Stebbins, Hoboken, NJ (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 14/980,130

(22) Filed: Dec. 28, 2015

(65) Prior Publication Data

US 2016/0128701 A1 May 12, 2016

Related U.S. Application Data

(62) Division of application No. 14/122,089, filed as application No. PCT/US2013/037758 on Apr. 23, 2013, now Pat. No. 9,220,518.

(60) Provisional application No. 61/644,214, filed on May 8, 2012.

(51) Int. Cl.
*A61F 5/00* (2006.01)
*A61B 17/15* (2006.01)
(Continued)

(52) U.S. Cl.
CPC ........... *A61B 17/15* (2013.01); *A61B 17/1739* (2013.01); *A61F 2/4202* (2013.01); *A61B 17/148* (2013.01); *A61B 2017/1775* (2013.01)

(58) Field of Classification Search
None
See application file for complete search history.

(56) References Cited

U.S. PATENT DOCUMENTS 9,220,518 B2    12/2015  Neal et al.
2005/0143745 A1*  6/2005  Hodorek ............ A61B 17/1659
                                                       606/87
(Continued)

FOREIGN PATENT DOCUMENTS

EP         1393696 A1      3/2004
FR         2715557 A1      8/1995
WO    WO-2013169475 A1    11/2013

OTHER PUBLICATIONS

"U.S. Appl. No. 14/122,089, Advisory Action mailed Jul. 21, 2015", 3 pgs.

(Continued)

*Primary Examiner* — Sameh Boles
(74) *Attorney, Agent, or Firm* — Schwegman Lundberg & Woessner, P.A.

(57) ABSTRACT

A method for implanting porous spacers (100) for foot and ankle fusion between separate bones of a joint or between two segments of a single bone following an osteotomy procedure. Such spacers may be used in conjunction with an ankle resection system which includes a resection frame (150 and a resection guide (1780). The resection frame can be anchored to the distal tibia and/or the talus and provides an opening (155) through which a bone cutting element can pass for cutting underlying bone. The resection guide can include one or more cutting slots (160,171,172) and the resection guide can be coupled to the resection frame with the one or more cutting slots positioned over the opening in the resection frame so that the bone cutting element can pass through the one or more cutting slots and through the opening in the resection frame for cutting the distal tibia and/or the talus.

14 Claims, 28 Drawing Sheets

(51) Int. Cl.
*A61F 2/42* (2006.01)
*A61B 17/17* (2006.01)
*A61B 17/14* (2006.01)

(56) References Cited

U.S. PATENT DOCUMENTS

| | | |
|---|---|---|
| 2008/0154270 A1 | 6/2008 | Haines et al. |
| 2010/0262150 A1 | 10/2010 | Lian |
| 2012/0109131 A1 | 5/2012 | Vasarhelyi et al. |
| 2014/0207143 A1 | 7/2014 | Lee et al. |
| 2015/0057665 A1 | 2/2015 | Neal et al. |

OTHER PUBLICATIONS

"U.S. Appl. No. 14/122,089, Final Office Action mailed May 12, 2015", 10 pgs.
"U.S. Appl. No. 14/122,089, Non Final Office Action mailed Feb. 4, 2015". 7 pgs.
"U.S. Appl. No. 14/122,089, Notice of Allowance mailed Aug. 17, 2015", 11 pgs.
"U.S. Appl. No. 14/122,089, Response filed Jan. 22, 2015 to Restriction Requirement mailed Dec. 28, 2014", 5 pgs.
"U.S. Appl. No. 14/122,089, Response filed Apr. 30, 2015 to Non Final Office Action mailed Feb. 4, 2015", 8 pgs.
"U.S. Appl. No. 14/122,089, Response filed Jul. 13, 2015 to Final Office Action mailed May 12, 2015", 8 pgs.
"U.S. Appl. No. 14/122,089, Restriction Requirement mailed Dec. 18, 2014", 7 pgs.
"International Application Serial No. PCT/US2013/037758, International Preliminary Report on Patentability mailed Nov. 20, 2014", 9 pgs.
"International Application Serial No. PCT/US2013/037758, International Search Report mailed Jun. 28, 2013", 6 pgs.
"International Application Serial No. PCT/US2013/037758, Written Opinion mailed Jun. 28, 2013", 7 pgs.

\* cited by examiner

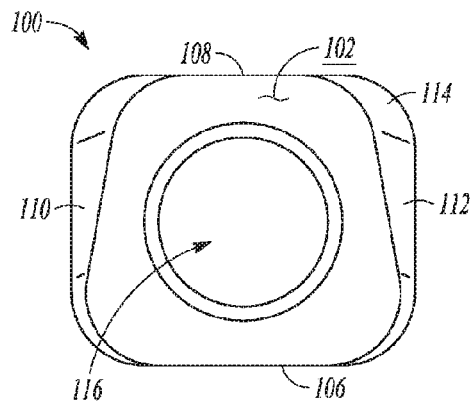
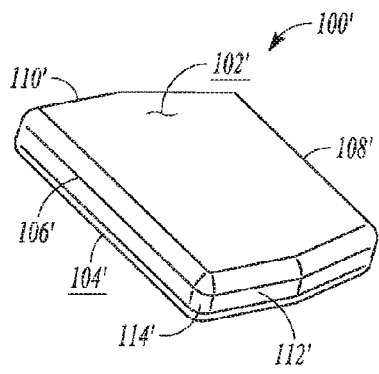
FIG. 3C          FIG. 3D
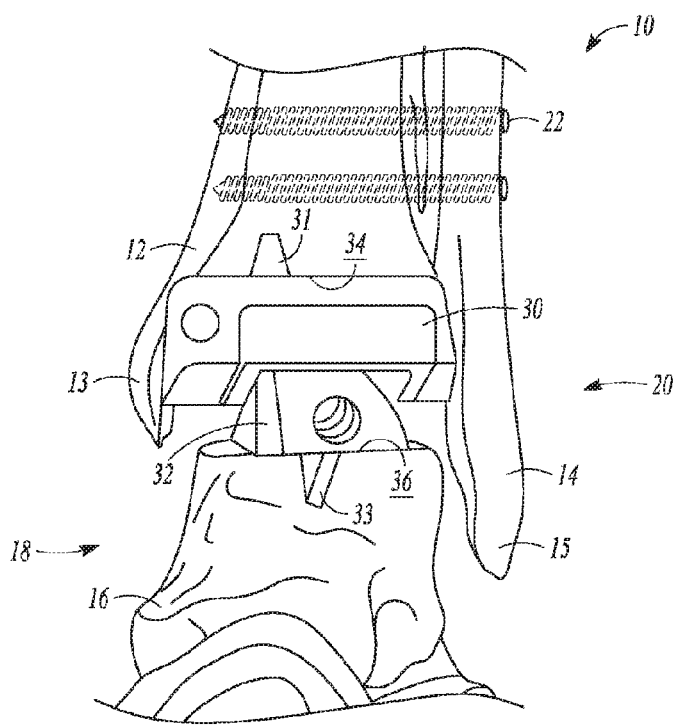
FIG. 4
(PRIOR ART)

POROUS SPACERS, INSTRUMENTS, AND METHODS FOR FOOT AND ANKLE FUSION

CLAIM OF PRIORITY

This application is a divisional of U.S. patent application Ser. No. 14/122,089, filed Nov. 25, 2013, now issued as U.S. Pat. No. 9,220,518 on Dec. 29, 2015, which application is a 371 National Stage Application of International Application Serial No. PCT/US2013/037758, filed Apr. 23, 2013, which application claims the benefit of U.S. Provisional Patent Application Ser. No. 61/644,214, filed on May 8, 2012, which are incorporated by reference herein in their entireties.

FIELD OF THE DISCLOSURE

The present disclosure relates to foot and ankle fusion. More particularly, the present disclosure relates to porous spacers for foot and ankle fusion, and to instruments and methods for performing the same.

BACKGROUND OF THE DISCLOSURE

Bone grafts are generally used for foot and ankle fusion procedures. However, bone grafts have limited strength. Because the ankle or foot must support a patients body weight, the bone graft may become physically overloaded when implanted in this part of a patient's body. Also, bone grafts may require intra-operative, custom shaping, which is time consuming and not readily reproducible.

SUMMARY

The present disclosure provides, in certain aspects, porous spacers for foot and ankle fusion. The porous spacers disclosed herein may be implanted between separate bones of a joint or between two segments of a single bone following an osteotomy procedure. The spacers can be used in conjunction with ancillary fixation devices such as intramedullary nails and/or bone plates. Another aspect of the present disclosure provides a bone resectioning system. The resectioning system can include a resection guide and a resection frame. When utilized in an ankle procedure, the resectioning system can be anchored to a proximal tibia and positioned over an ankle joint. After securing the resection frame-resection guide combination over the ankle joint, the talus and tibia can be resected using one or more cutting slots, surfaces, or guides of the resection guide. After making one or more cuts, the resection guide, which is situated over an opening in the resection frame, can be moved away from this opening allowing a surgeon to check the fit of a fusion spacer or provisional spacer while the resection frame is still secured to bone. After checking a fit, if more bone needs to be cut, the surgeon simply moves the resection guide back into position over the opening in the resection frame or replaces if with a different guide that may now be deemed more suitable to continue the procedure. This method of resection can be performed on various joints and bones in the anatomy.

According to an embodiment of the present disclosure, a method is provided for fusing a patient's joint. The joint includes a first bone having a first joint surface and a second bone having a second joint surface that articulates with the first joint surface. The method includes the steps of: resecting the first joint surface of the first bone of the joint, the first bone being anatomically located in the patient's foot or ankle; resecting the second joint surface of the second bone of the joint; and implanting a fusion spacer between the resected first and second bones to fuse the first and second bones, wherein the fusion spacer is constructed of a metal-coated scaffold.

According to another embodiment of the present disclosure, a method is provided for fusing a bone cut during an osteotomy procedure. Such a method can be used in conjunction with any suitable osteotomy procedure including those involving removing a segment of a bone, making a cut to divide the bone or cutting a bone to change the angle or axis of a bone. The method includes the steps of: resecting a bone into a first bone segment and a second bone segment, for example where the bone is anatomically located in the patient's foot or ankle; and implanting a fusion spacer between the resected first and second bone segments to fuse the first and second bone segments, wherein the fusion spacer in one particular illustrative aspect is constructed of a metal-coated scaffold.

According to another embodiment of the present disclosure, a method is provided for fusing a patient's ankle joint to fill bone voids such as following removal of a prosthetic tibial component from the patient's tibia and removal of a prosthetic talar component from the patient's talus. The method includes the steps of: providing a fusion spacer having a proximal surface, a distal surface, a substantially flat anterior wall, a substantially flat posterior wall, a substantially flat medial wall, and a substantially Out lateral wall, the substantially flat walls cooperating to define a block-shaped fusion spacer; and implanting the fusion spacer between the patient's tibia and the patient's talus into a space once occupied by the prosthetic tibial component and the prosthetic talar component with the proximal surface of the fusion spacer contacting the patient's tibia and the distal surface of the fusion spacer contacting the patient's talus.

According to another embodiment of the present disclosure, a fusion spacer is provided including a metal-coated scaffold having a proximal surface, a distal surface, and at least one outer wall between the proximal surface and the distal surface, the at least one outer wall widening distally from the proximal surface to an apex and narrowing distally from the apex to the distal surface.

According to another embodiment of the present disclosure, a fusion spacer is provided including a metal-coated scaffold having a first bone-contacting surface and a second bone-contacting surface, at least one of the first and second bone-contacting surfaces having a concave curvature to engage a convex bone surface.

According to another embodiment of the present disclosure a resectioning device is provided including a resection guide and a resection frame. The resection frame is configured to be attached to a bone for an osteotomy or attached to opposing bones of a joint. The resection guide is coupled to the resection frame and includes one or more cutting slots.

According to another embodiment of the present disclosure an ankle joint resectioning system is provided including an anchor assembly, a resection frame and a resection guide. The resection frame can be attached to the distal end of the tibia as well as to the talus. The resection guide can be coupled to the resection frame and can include one or more cutting slots.

According to another embodiment of the present disclosure a method of resecting bone is provided. In one step, a resection frame is positioned over bone. In another step, a resection guide is coupled to the resection frame. Thereafter, a bone cutting element is passed through a first cutting slot in the resection guide and through an opening in the resection frame to make a cut in underlying bone. The resection guide can include one or more cutting slots through which the bone cutting element passes.

According to another embodiment of the present disclosure a method for placing a bone implant or a provisional bone implant is provided. In one step, a resection frame is anchored to bone where the resection frame includes an opening through which the bone implant or the provisional bone implant can pass. In another step, a resection guide is positioned over the opening in the resection frame where such positioning blocks passage of the bone implant or the provisional bone implant through the opening in the resection frame while allowing passage of a bone cutting element through the resection guide and through the opening in the resection frame to cut underlying bone. Thereafter, a space is created for the bone implant or the provisional bone implant which includes passing a bone cutting element through a first cutting slot in the resection guide and through the opening in the resection frame and into underlying bone. The resection guide can then be repositioned with respect to the opening in the resection frame such that the bone implant or the provisional bone implant can be passed through the opening in the resection frame. The method can also include passing the bone implant or the provisional bone implant through the opening in the resection frame and into the space.

To better understand the porous spacers, instruments, and methods for foot and ankle fusion disclosed herein, anon-limiting list of examples is provided here:

In Example 1, an ankle resection system can comprise a resection frame and a resection guide and optionally a proximal tibial anchor. The resection frame is anchorable to the distal tibia and/or the talus and provides an opening through which a bone cutting element can pass for cutting underlying bone. When present, the proximal tibial anchor can be connected to the resection frame. The resection guide can include one or more cutting slots, and the resection guide can be coupled to the resection frame with the one or more cutting slots positioned over the opening in the resection frame so that the bone cutting element can pass through the one or more cutting slots and through the opening in the resection frame for cutting the distal tibia and/or the talus.

In Example 2, the ankle resection system of Example 1 can optionally be configured such that the resection frame being connected to the proximal tibial anchor comprises a separate elongated rod coupled to the proximal tibial anchor and the resection frame.

In Example 3, the ankle resection system of Example 2 can optionally be configured such that the proximal tibial anchor includes a hollow tubular section in which a proximal end of the elongated rod is slidably received to permit adjustment of the distance between the proximal tibial anchor and the resection frame.

In Example 4, the ankle resection system of any one or any combination of Examples 2 or 3 can optionally be configured such that a proximal end of the elongated rod is coupled to the proximal tibial anchor so as to permit adjustment of the proximal end in a medial-lateral direction with respect to the proximal tibial anchor.

In Example 5, the ankle resection system of any one or any combination of Examples 2-4 can optionally be configured such that a distal end of the elongated rod is coupled to the resection frame so as to permit adjustment of the distal end in an anterior-posterior direction with respect to the resection frame.

In Example 6, the ankle resection system of any one or any combination of Examples 1-5 can optionally be configured such that the resection guide and the resection frame are translatable relative to one another in a longitudinal direction for repositioning the one or more cutting slots over the opening in the resection frame.

In Example 7, the ankle resection system of Example 6 can optionally be configured such that the one or more cutting slots includes a medial cutting slot and a lateral cutting slot.

In Example 8, the ankle resection system of any one or any combination of Examples 1-7 can optionally be configured such that the resection frame comprises a first talus pin aperture with a longitudinal axis that extends in a direction non-parallel to a longitudinal axis of a second talus pin aperture.

In Example 9, the ankle resection system of any one or any combination of Examples 1-8 can optionally be configured such that the resection. frame includes a proximal body portion with a medial leg and a lateral leg of the resection frame extending from the proximal body portion, and with the opening in the resection frame extending between the medial leg and the lateral leg, In Example 10, the ankle resection system of Example 9 can optionally be configured such that the resection guide extends over the medial lee and the lateral leg with a posterior body portion of the resection guide extending down into the opening in the resection frame.

In Example 11, a method for resecting bone comprises positioning a resection frame over bone, the resection frame including an opening through which a bone cutting element can pass; coupling a resection guide to the resection frame, the resection guide including one or more cutting slots through which the bone cutting element can pass; and passing a bone cutting element through a first cutting slot in the resection guide and through the opening in the resection frame to make a cut in underlying bone.

in Example 12, the method of Example 11 can optionally further comprise anchoring the resection frame to bone.

in Example 13, the method of Example 12 can optionally be configured such that the coupling occurs after the anchoring.

In Example 14, the method of any one or any combination of Examples 12 or 13 can optionally be configured such that the resection guide is decoupled from the resection frame with the resection frame remaining anchored to bone.

In Example 15, the method of Example 14 can optionally be configured such that the resection guide being decoupled from the resection frame uncovers the opening in the resection frame to permit a bone implant or a provisional bone implant to pass through the opening in the resection frame for placement in underlying bone.

In Example 16, the method of any one or any combination of Examples 11-15 can optionally be configured such that the cut in underlying bone occurs on a first side of a joint, and wherein a further cut in underlying bone is made on a second side of the joint.

In Example 17, the method of Example 16 can optionally be configured such that the joint is an ankle joint.

in Example 18, the method of Example 17 can optionally further comprise connecting the resection frame to a proximal tibial anchor.

In Example 19, a method for placing a bone implant or a provisional bone implant, comprises anchoring a resection frame to bone, the resection frame including an opening through which the bone implant or the provisional bone implant can pass; positioning a resection guide over the opening in the resection frame, the positioning blocking passage of the bone implant or the provisional bone implant through the opening in the resection frame while allowing passage of a bone cutting element through the resection guide and through the opening in the resection frame to cut underlying bone; creating a space for the bone implant or the provisional bone implant which includes passing a bone cutting element through a first cutting slot in the resection guide and through the opening in the resection frame and into underlying bone; repositioning the resection guide with respect to the opening in the resection frame such that the bone implant or the provisional bone implant can be passed through the opening in the resection frame; and passing the bone implant or the provisional bone implant through the opening in the resection frame and into the space.

In Example 20, the method of Example 19 can optionally be configured such that the positioning includes reversibly locking the resection guide to the resection frame.

In Example 21, the method of Example 20 can optionally be configured such that the reversibly locking occurs before the anchoring.

In Example 22, the method of any one or any combination of Examples 20-21 can optionally be configured such that the repositioning includes unlocking and separating the resection guide from the resection frame.

In Example 23, the method of any one or any combination of Examples 19-22 can optionally be configured such that the resection frame includes a proximal body portion with a medial leg and a lateral leg of the resection frame extending from the proximal body portion, and with the opening in the resection frame extending between the medial leg and the lateral leg.

In Example 24, the method of any one or any combination of Examples 19-23 can optionally be configured such that the space is situated around an ankle joint.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein:

FIG. 3C is a proximal plan view of the first fusion spacer of FIG. 3B;

FIG. 3D is a perspective view of another fusion spacer that is similar to the first fusion spacer of FIG. 3C;

FIG. 4 is an anterior elevational view of a patient's ankle joint with a prosthetic tibial component and a prosthetic talar component implanted therein;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

The present disclosure relates to spacers for foot and ankle fusion. Each fusion spacer is anatomically shaped for implantation in a particular anatomic location of the foot or ankle Each spacer shape may be available in different sizes (e.g., different anterior-posterior dimensions, different medial-lateral dimensions, different superior-inferior dimensions) to accommodate a variety of different patients.

1. Highly Porous Construction

According to an exemplary embodiment of the present disclosure, the fusion spacers of the present disclosure are constructed of a highly porous biomaterial. A highly porous biomaterial is useful as a bone substitute and as cell and tissue receptive material. A highly porous biomaterial may have a porosity as low as 55%, 65%, or 75% or as high as 80%, 85%, or 90%.

An example of such a material is produced using Trabecular Metal™ Technology generally available from Zimmer. Inc., of Warsaw. Ind. Trabecular Metal™ is a trademark of Zimmer. Inc. Such a material may be a metal-coated scaffold that is formed from a reticulated vitreous carbon foam scaffold or substrate which is infiltrated and coated with a biocompatible metal, such as tantalum, by a chemical vapor deposition ("CVD") process in the manner disclosed in detail in U.S. Pat. No. 5,282,861 to Kaplan and U.S. Pat. No. 6,103,149 to Stankiewiez, the entire disclosures of which are expressly incorporated herein by reference. In addition to tantalum, other metals such as niobium, or alloys of tantalum and niobium with one another or with other metals may also be used.

Figure 3A:
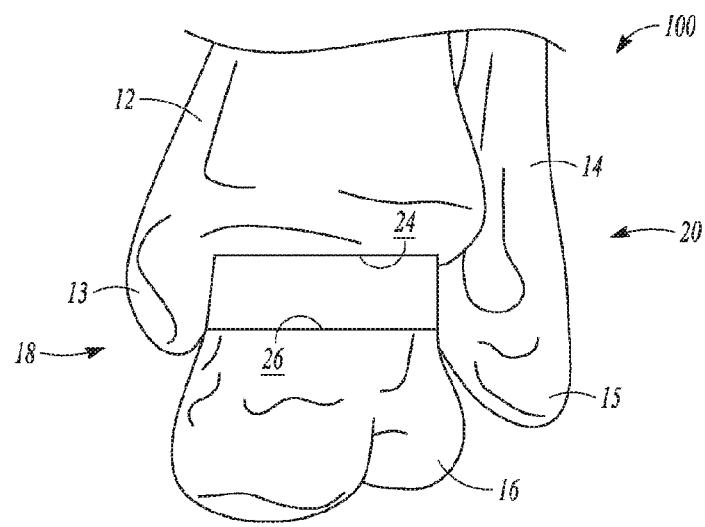
FIG. 3A is an anterior elevational view of a patients resected ankle joint.
Figure 3B:
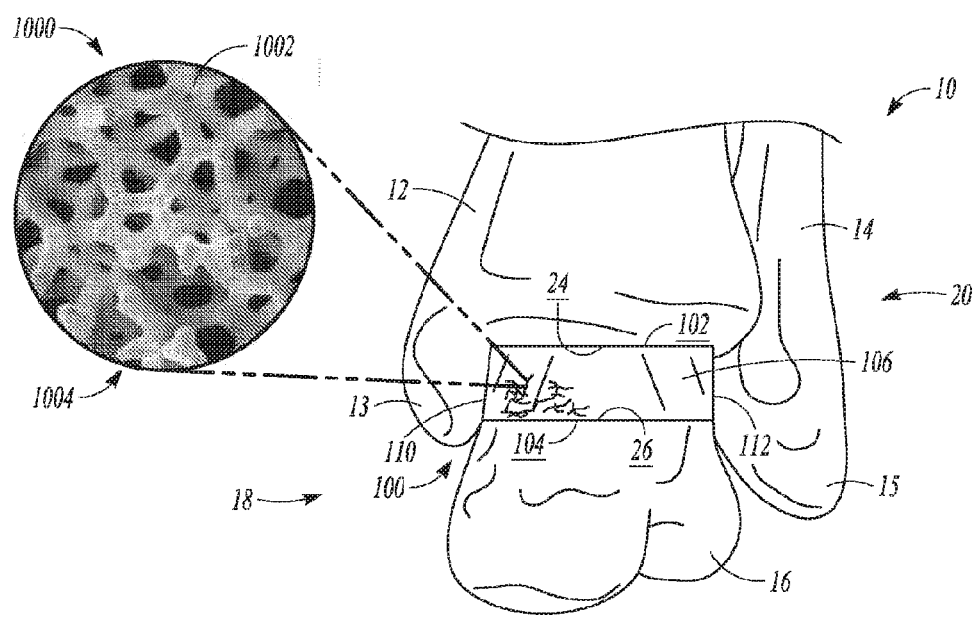
FIG. 3B is an anterior elevational view of the resected ankle joint of FIG. 3A with a first exemplary fusion spacer implanted therein to fuse the ankle joint.

An exemplary porous tantalum material 1000 is shown in FIG. 3B, Generally, the porous tantalum material 1000 includes a large plurality of ligaments 1002 defining open spaces or pores 1004 there between, with each ligament 1002 generally including a carbon core covered by a thin film of metal such as tantalum, for example. The open spaces 1004 between the ligaments 1002 form a matrix of continuous channels having no dead ends, such that growth of cancellous bone through the porous tantalum structure 1000 is uninhibited. The porous tantalum structure 1000 may include up to 75%, 85%, or more void space therein. Thus, the porous tantalum structure 1000 may be substantially uniform and consistent in composition and may closely resemble the structure of natural cancellous bone, thereby providing a matrix into which cancellous bone may grow to provide fixation of the fusion spacer to the patient's bone.

The porous tantalum structure 1000 may be made in a variety of densities in order to selectively tailor the structure for particular applications. In particular, as discussed in the above-incorporated U.S. Pat. No. 5,282,861, the porous tantalum structure 1000 may be fabricated to virtually any desired porosity and pore size, and can thus be matched with the surrounding natural bone in order to provide an improved matrix for bone ingrowth and mineralization.

In addition to providing a matrix for bone ingrowth, the metal-coated ligaments 1002 of the porous tantalum structure 1000 provide a permanent source of strength and support to the bone. The metal-coated ligaments 1002 do not degrade or absorb into the body, but rather the metal-coated ligaments 1002 remain intact to support the bone. Although strong, the porous tantalum structure 1000 is also lightweight.

The porous tantalum structure 1000 is also readily shapeable. In one embodiment, the reticulated vitreous carbon foam substrate is shaped before being infiltrated and coated with metal, such as by crushing the substrate in a mold. In another embodiment, the material is shaped after being infiltrated and coated with metal, such as by machining. These shaping processes may be performed preoperatively and under automatic or controlled conditions.

Bone growth factors, therapeutic agents, medications, and other materials may be incorporated into the porous tantalum structure 1000 to promote healing and bone fusion. An example of such a material is the CopiOs® Bone Void Filler which is available from Zimmer. Inc., of Warsaw. Indiana, CopiOs® is a registered trademark of Zimmer. Inc. Other suitable materials are described in U.S. Pat. No. 5,290,763 to Poser et al., U.S. Pat. No. 7,718,616 to Thorne, and U.S. Patent Application Publication No. 2011/0165199 to Thorne, the entire disclosures of which are expressly incorporated herein by reference.

2. Joint Spacers

In one embodiment, the fusion spacers disclosed herein may be implanted between separate bones of a joint, such as between articulating bones of a mobile joint or abutting bones of an immobile joint. One or more of the interfacing bone surfaces of the joint may require resection to receive the spacer. The resection may remove the hard, outer layer of cortical bone from the interfacing surface and expose the soft, inner layer of cancellous bone beneath the interfacing surface to receive the spacer. The resection may also alter the shape of the interfacing surface to receive the spacer.

a. Ankle Joint

Figure 1:
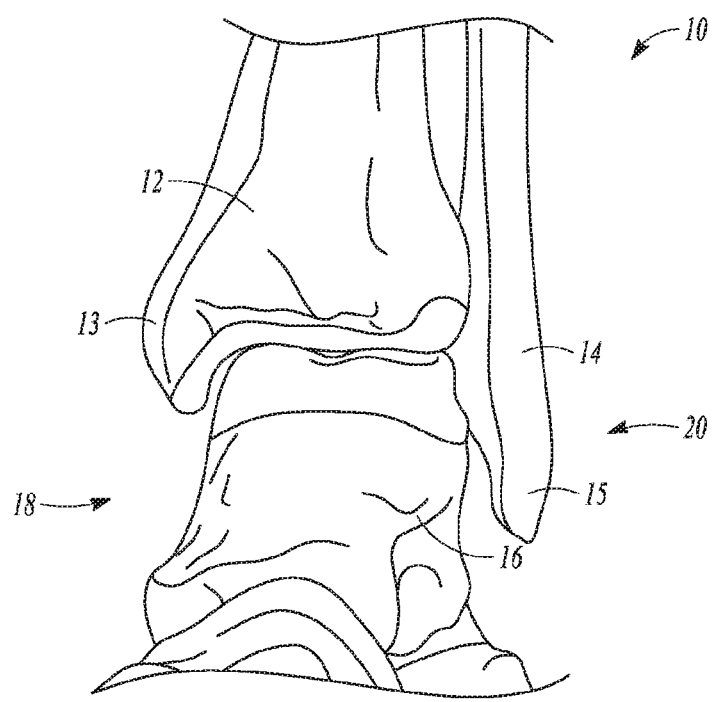
FIG. 1 is an anterior elevational view of a patient's healthy ankle joint.

Referring initially to FIG. 1, a patient's healthy ankle or tibiotalar joint 10 is shown. Ankle joint 10 includes three bones: tibia 12, fibula 14, and talus 16. In use, talus 16 articulates relative to tibia 12 and fibula 14. On medial side 18 of ankle joint 10, tibia 12 includes an enlarged distal end known as the medial malleolus 13. On lateral side 20 of ankle joint 10, fibula 14 includes an enlarged distal end known as the lateral malleolus 15. Medial malleolus 13 and lateral malleolus 15 cooperate to support and stabilize talus 16 there between.

If ankle joint 10 develops arthritis, deteriorates, suffers traumatic injury, or becomes otherwise damaged, it may be necessary to perform a joint fusion procedure to prevent further articulation of ankle joint 10. The fused ankle joint 10 becomes rigid and immobile, like a single bone.

Figure 2:
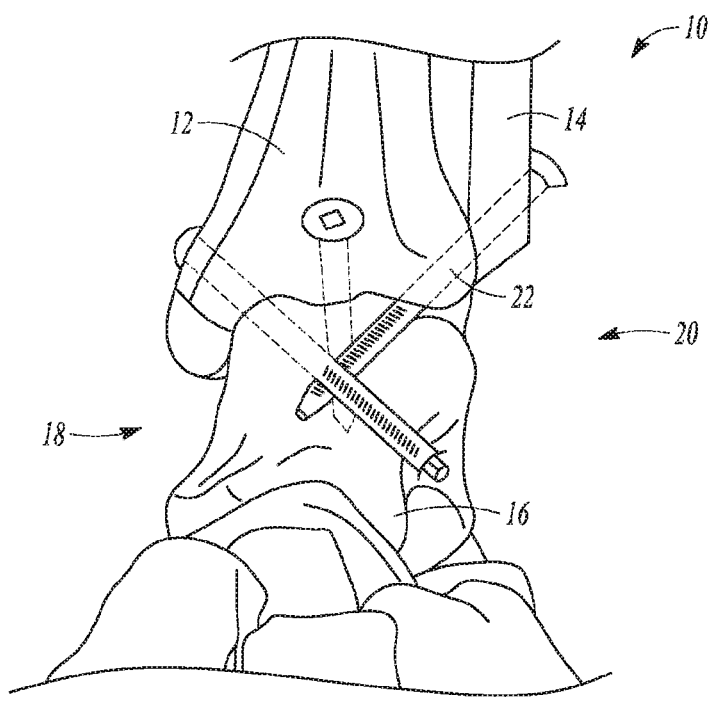
FIG. 2 is an anterior elevational view of a patients ankle joint with screws implanted therein to fuse the ankle joint.

Traditionally, ankle joint 10 was fused by driving a plurality of screws 22 through tibia 12 and fibula 14 and into talus 16, as shown in FIG. 2. Screws 22 would prevent further articulation of talus 16 relative to tibia 12 and fibula 14. To accommodate screws 22, certain fusion procedures required resection of medial malleolus 13 and/or lateral malleolus 15.

In FIGS. 3A-3C, a first exemplary fusion spacer 100 is provided in the form of an arthrodesis spacer. As shown in FIG. 3B, fusion spacer 100 may be constructed entirely or substantially entirely of a highly porous biomaterial 1000 in the form of a metal-coated scaffold, which is described further above.

Ankle joint 10 may be prepared to receive fusion spacer 100 by resecting tibia 12 along resected surface 24 and talus 16 along resected surface 26. Resected surfaces 24, 26 are illustratively planar, parallel surfaces. In an exemplary embodiment, medial malleolus 13 and/or lateral malleolus 15 may be retained to continue supporting ankle joint 10, unlike FIG. 2.

Fusion spacer 100 is a generally block-shaped structure having proximal surface 102 and distal surface 104. Like resected surfaces 24, 26 of ankle joint 10, surfaces 102, 104 of fusion spacer 100 are illustratively planar, parallel surfaces. Fusion spacer 100 also includes anterior wall 106, posterior wall 108, medial wall 110, and lateral wall 112 that are substantially flat and that come together at rounded or curved edges 114, As shown in FIG. 3C, fusion spacer 100 includes a hollow interior 116 that may be configured to receive a bone graft, an osteoconductive scaffold (e.g., CopiOs® Bone Void Filler), bone cement, or a fastener, for example.

Proximal surface 102 of fusion spacer 100 corresponds to resected surface 24 of tibia 12, as shown in FIG. 3B. For example, in FIG. 3C, proximal surface 102 of fusion spacer 100 is trapezoidal in shape and narrows posteriorly (i.e., toward posterior wall 108) to mimic the trapezoidal shape of resected surface 24 of tibia 12. Also, in FIG. 3C, proximal surface 102 is larger in medial-lateral width (i.e., the distance between medial wall 110 and lateral wall 112) than in anterior-posterior depth (i.e., the distance between anterior wall 106 and posterior wall 108). When implanted, proximal surface 102 of fusion spacer 100 may span across the soft, inner layer of cancellous bone to the hard, outer layer of cortical bone at resected surface 24 of tibia 12.

Distal surface 104 of fusion spacer 100 corresponds to resected surface 26 of talus 16, as shown in FIG. 3B. For example, in FIG. 3C, distal surface 104 (not shown) of fusion spacer 100 is rectangular in shape to mimic the rectangular shape of resected surface 26 of talus 16. Also, in FIG. 3C, distal surface 104 of fusion spacer 100 is larger than proximal surface 102 of fusion spacer 100. As a result, fusion spacer 100 widens distally from proximal surface 102 to distal surface 104, with anterior wall 106, posterior wall 108, medial wall 110, and lateral wall 112 angling outward from proximal surface 102 to distal surface 104. When implanted, distal surface 104 of fusion spacer 100 may span across the soft, inner layer of cancellous bone to the hard, outer layer of cortical bone at resected surface 26 of talus 16.

According to an exemplary embodiment of the present disclosure, fusion spacer 100 has a highly porous construction at least along proximal surface 102 and digtal surface 104. In this manner, fusion spacer 100 may encourage bone ingrowth from tibia 12 into proximal surface 102 and from talus 16 into distal surface 104, thereby fusing tibia 12 and talus 16 via fusion spacer 100. According to another exemplary embodiment of the present disclosure, fusion spacer 100 is entirely porous in construction to encourage uninterrupted bone ingrowth from tibia 12 and talus 16.

Fusion spacer 100 may be provided in various sizes to accommodate a variety of different patients. For example, a set of three fusion spacers 100 may be provided having distal surfaces 104 of various sizes (e.g., small, medium, and large). The small size distal surface 104 may have a medial-lateral width of any suitable value including any value within the range of about 25-30 mm, such as a medial-lateral width of about 28 mm. The small size distal surface 104 may have an anterior-posterior depth of any suitable value including any value within the range of about 20-25 mm, such as an anterior-posterior depth of about 22 mm. The medium size distal surface 104 may have a medial-lateral width of any suitable value including any value within the range of about 28-33 mm, such as a medial-lateral width of about 30 mm. The medium size distal surface 104 may have an anterior-posterior depth of any suitable value including any value within the range of about 20-30 mm, such as an anterior-posterior depth of about 22 mm. The large size distal surface 104 may have a medial-lateral width of any suitable value including any value within the range of about 30-37 mm, such as a medial-lateral width of about 32 mm. The large size distal surface 104 may have an anterior-posterior depth of any suitable value including any value within the range of about 20-33 mm, such as an anterior-posterior depth of about 22 mm. Each fusion spacer 100 may also be available in different proximal-distal thicknesses (i.e., the distance between proximal surface 102 and distal surface 104), such as about 5 mm and about 10 mm. The set may include other fusion spacers 100 in addition to those described herein.

In FIG. 3D, another fusion spacer 100' is provided that is similar to the above-described fusion spacer 100, with like reference numbers indicating like elements, except as described below. Fusion spacer 100' is solid, while the above-described fusion spacer 100 is hollow. Also, fusion spacer 100' has a relatively thin proximal-distal thickness (e.g., 5 mm), while the above-described fusion spacer 100 has a relatively thick proximal-distal thickness (e.g., 10 mm). Furthermore, distal surface 104' of fusion spacer 100' is trapezoidal in shape, like proximal surface 102', while distal surface 104 of the above-described fusion spacer 100 is rectangular in shape.

Rather than fusing the ankle joint 10, as shown in FIG. 2, a surgeon may choose to maintain mobility of the ankle joint 10 by performing a total ankle replacement ("TAR") procedure. As shown in FIG. 4, TAR involves replacing the distal tibia 12 with a prosthetic tibial component 30 and the proximal talus 16 with a prosthetic talar component 32. The prosthetic tibial component 30 rests against resected surface 34 of tibia 12, with post 31 of the prosthetic tibial component 30 extending beyond resected surface 34 and into tibia 12. The prosthetic talar component 32 rests against resected surface 36 of talus 16, with post 33 extending b yond resected surface 36 and into talus 16. Resected surfaces 34, 36 are illustratively planar, parallel surfaces. In an exemplary embodiment, medial malleolus 13 and/or lateral malleolus 15 may be retained to supporting ankle joint 10. Patient-specific guides and methods for preparing resected surfaces 34, 36 of ankle joint 10 are described further in U.S. patent application Ser. No. 13/050,190 to Li, filed Mar. 17, 2011, the entire disclosure of which is expressly incorporated herein by reference.

Figure 5A:
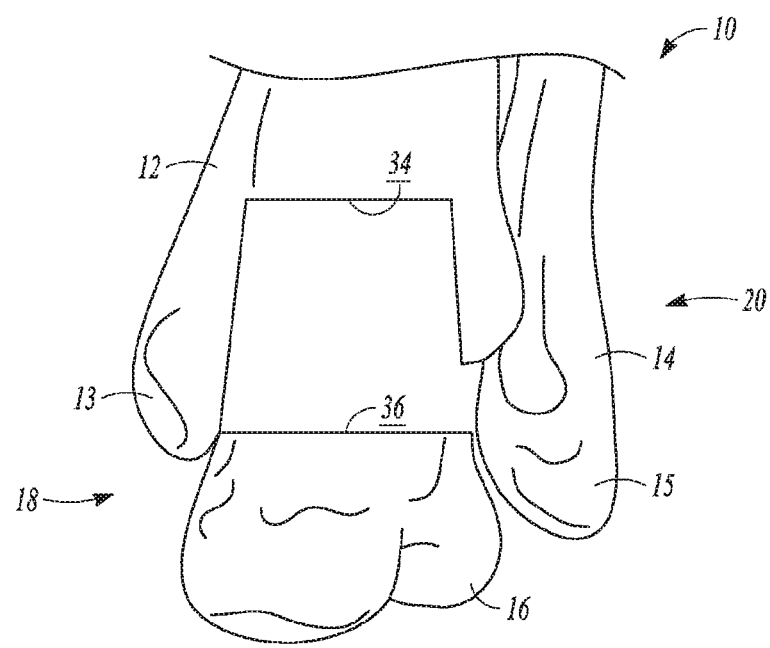
FIG. 5A is an anterior elevational view of the patient's ankle joint after removal of the prosthetic tibial component and the prosthetic talar component of FIG. 4.

In certain situations, the TAR procedure may fail, such as in patients suffering from infection or severe pain, for example. Therefore, it may become necessary to remove the prosthetic tibial component 30 and the prosthetic talar component 32 from the patient's ankle joint 10 and proceed with fusion of the patient's ankle joint 10. As shown in FIG. 5A, this removal leaves behind a large empty space between tibia 12 and talus 16 that was once occupied by the prosthetic tibial component 30 and the prosthetic talar component 32.

Figure 5B:
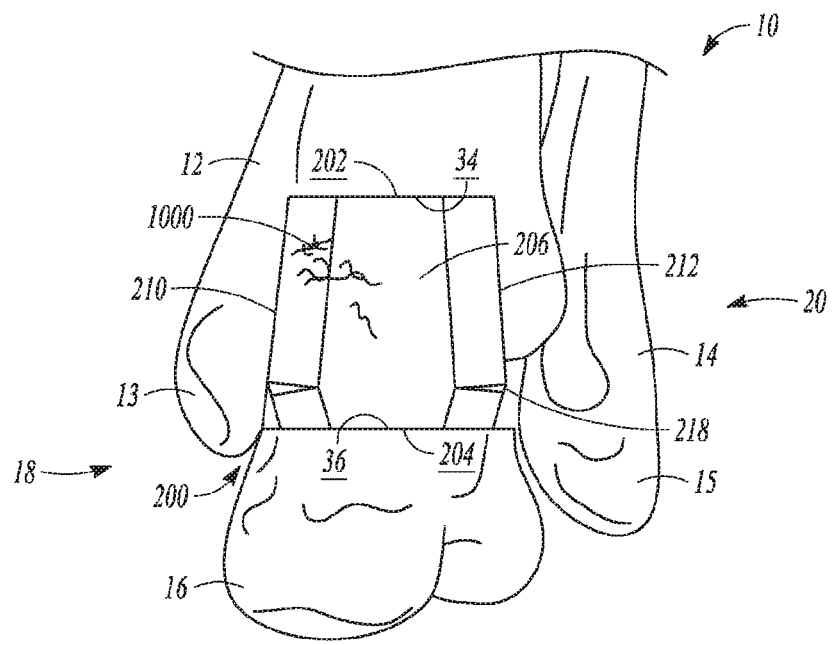
FIG. 5B is an anterior elevational view of the ankle joint of FIG. 5A with a second exemplary fusion spacer implanted therein to fuse the ankle joint.
Figure 5C:
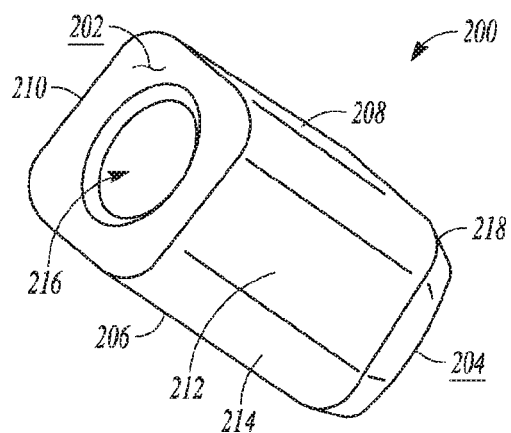
FIG. 5C is a perspective view of the second fusion spacer of FIG. 5B.

In FIGS. 5A-5C, a second exemplary fusion spacer 200 is provided in the form of a TAR revision implant. Fusion spacer 200 may be constructed entirely or substantially entirely of a highly porous biomaterial 1000 in the form of a metal-coated scaffold, as described further above and as shown in FIG. 3B.

After removing the prosthetic tibial component 30 and the prosthetic talar component 32 (FIG. 4), resected surfaces 34, 36 of ankle joint 10 may be capable of receiving fusion spacer 200 with little or no additional bone removal. Also, medial malleolus 13 and/or lateral malleolus 15 may be retained to support ankle joint 10. In addition to being used in TAR revision procedures, as previously described, fusion spacer 200 may also be used in primary fusion procedures involving severe bone loss.

Fusion spacer 200 is a generally block-shaped structure having proximal surface 202 and distal surface 204. Like resected surfaces 34, 36 of ankle joint 10, surfaces 202, 204 of fusion spacer 200 are illustratively planar, parallel surfaces. Fusion spacer 200 also includes anterior wall 206, posterior wall 208, medial wall 210, and lateral wall 212 that are substantially flat and that come together at rounded or curved edges 214. As shown in FIG. 5C, fusion spacer 200 includes a hollow interior 216 that may be configured to receive a bone graft, an osteoconductive scaffold (e.g., CopiOs®) Bone Void Filler), bone cement, or a fastener, for example.

Proximal surface 202 of fusion spacer 200 corresponds to resected surface 34 of tibia 12, as shown in FIG. 5B. For example, in FIG. 5C, proximal surface 202 of fusion spacer 200 is trapezoidal in shape and narrows posteriorly (i.e., toward posterior wall 208) to mimic the trapezoidal shape of resected surface 34 of tibia 12. Also, proximal surface 202 is illustratively larger in medial-lateral width (i.e., the distance between medial wall 210 and lateral watt 212) than in anterior-posterior depth (i.e., the distance between anterior wall 206 and posterior wall 208), When implanted, proximal surface 202 of fusion spacer 200 may span across the soft, inner layer of cancellous bone to the hard, outer layer of cortical bone at resected surface 34 of tibia 12.

Distal surface 204 of fusion spacer 200 corresponds to resected surface 36 of talus 16, as shown in FIG. 5B. For example, in FIG. 5C, distal surface 204 of fusion spacer 200 is trapezoidal in shape and narrows posteriorly (i.e., toward posterior wall 208) to mimic the trapezoidal shape of resected surface 36 of talus 16. To fill the space between tibia 12 and talus 16, fusion spacer 200 may widen distally from proximal surface 202 toward distal surface 204, with anterior wall 206, posterior wall 208, medial wall 210, and lateral wall 212 angling outward from proximal surface 202. However, to limit impingement near distal surface 204, fusion spacer 200 may transition from widening distally to narrowing distally along apex 218. When implanted, distal surface 204 of fusion spacer 200 may span across the soft, inner layer of cancellous bone to the hard, outer layer of cortical bone at resected surface 36 of talus 16.

Distal surface 204 of fusion spacer 200 may be similar to distal surface 104 of the above-described fusion spacer 100 (FIGS. 3A-3C), because both are configured to rest against the resected talus 16. However, because fusion spacer 200 accounts for a larger amount of removed bone, fusion spacer 200 may have a larger proximal-distal thickness than the above-described fusion spacer 100.

According to an exemplary embodiment of the present disclosure, fusion spacer 200 has a highly porous construction at least along proximal surface 202 and distal surface 204. In this mariner, fusion spacer 200 may encourage bone ingrowth from tibia 12 into proximal surface 202 and from talus 16 into distal surface 204, thereby fusing tibia 12 and talus 16 via fusion spacer 200. According to another exemplary embodiment of the present disclosure, fusion spacer 200 is entirely porous in construction to encourage uninterrupted bone ingrowth from tibia 12 and talus 16.

Fusion spacer 200 may be provided in various sizes to accommodate a variety of different patients. For example, a set of three fusion spacers 200 may be provided having distal surfaces 204 of various sizes (e.g., small, medium, and large). The small size distal surface 204 may have a medial-lateral width of any suitable value including any value within the range of about 25-30 mm, such as a medial-lateral width of about 28 mm. The small size distal surface 204 may have an anterior-posterior depth of any suitable value including any value within the range of about 20-27 mm, such as an anterior posterior depth of about 25 mm. The medium size distal surface 204 may have a medial-lateral width of any suitable value including any value within the range of about 27-33 mm, such as a medial-lateral width of about 30 mm. The medium size distal surface 204 may have an anterior-posterior depth of any suitable value including any value within the range of about 25-30 mm, such as an anterior-posterior depth of about 28 mm. The large size distal surface 204 may have a medial-lateral width of any suitable value including any value within the range of about 30-37 min, such as a medial-lateral width of about 32 mm. The large size distal surface 204 may have an anterior-posterior depth of any suitable value including any value within the range of about 27-33 mm, such as an anterior-posterior depth of about 30 mm. Each fusion spacer 200 may also be available in different proximal-distal thicknesses (i.e., the distance between proximal surface 202 and distal surface 204), such as about 20 mm, about 25 mm, about 30 mm, about 35 mm, and about 40 mm. Thus may include other fusion spacers 200 in addition to those described herein.

Figure 5D:
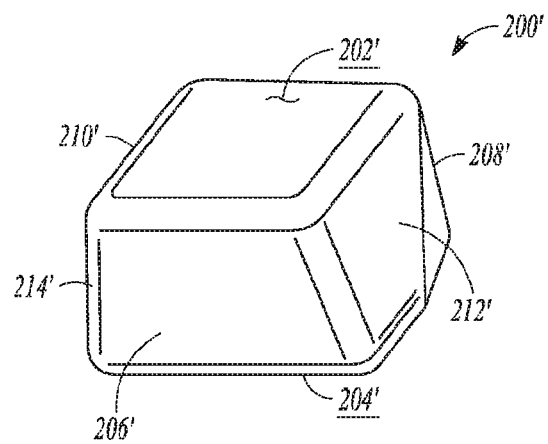
FIGS. 5D-5G are perspective views of other fusion spacers that can be used in a similar manner as the second fusion spacer of FIG. 5C.

In FIG. 5D, another fusion spacer 200' is provided that is similar to the above-described fusion spacer 200, with like reference numbers indicating like elements, except as described below. Fusion spacer 200' is solid, while the above-described fusion spacer 200 is hollow. Also, fusion spacer 200' has a relatively thin proximal-distal thickness (e.g., 25 mm), while the above-described fusion spacer 200 has a relatively thick proximal-distal thickness (e.g., 35 mm).

Figure 5E:
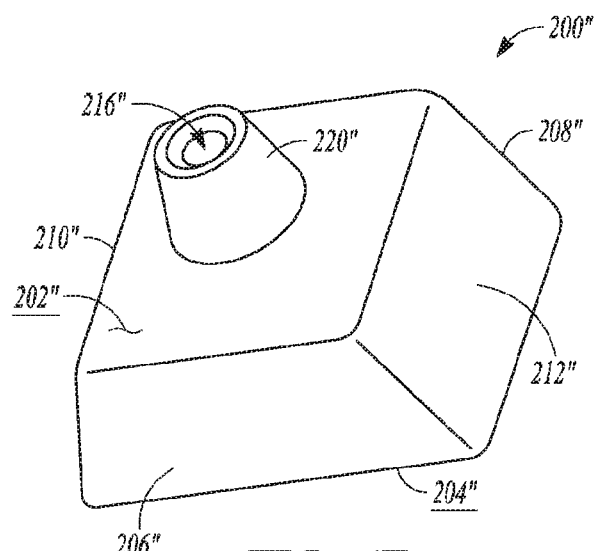

In FIG. 5E, another fusion spacer 200" is provided that is similar to the above-described fusion spacer 200, with like reference numbers indicating like elements, except as described below. Fusion spacer 200" includes stem 220" that extends proximally from proximal surface 202". When implanted with proximal surface 202" of fusion spacer 200" positioned against resected surface 34 of tibia 12 (FIG. 5B), stem 220" may extend beyond resected surface 34 and into the space once occupied by post 31 of the prosthetic tibial component 30 (FIG. 4).

Figure 5F:
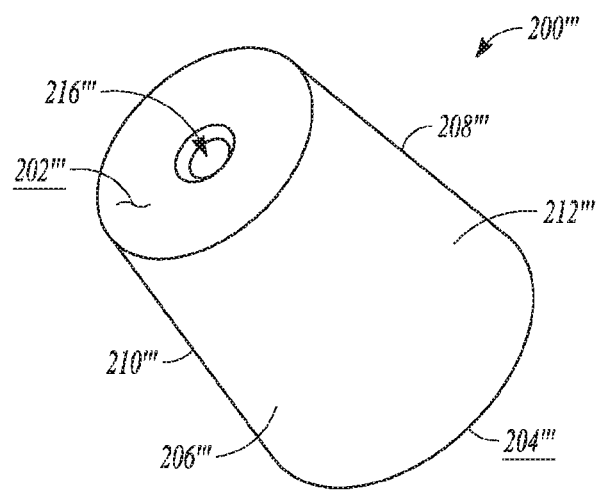
Figure 5G:
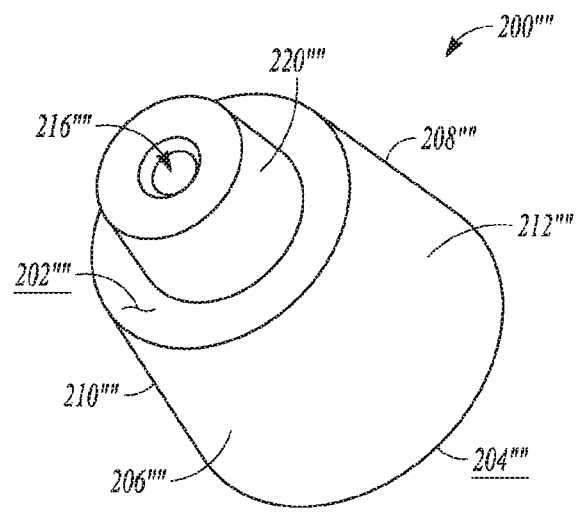

In FIGS. 5F and 5G, other fusion spacers 200''', 200'''' are provided that are similar to the above-described fusion spacer 200, with like reference numbers indicating like elements, except as described below. Fusion spacers 200''', 200'''' are generally conical-shaped structures, while the above-described fusion spacer 200 is a generally block-shaped structure. With respect to fusion spacer 200''', for example, anterior wall 206''', posterior wall 208''', medial wall 210''', and lateral wall 212''' cooperate to define the generally conical-shaped structure. Additionally, fusion spacer 200'''' of FIG. 5G includes stem 220'''' that extends proximally from proximal surface 202'''', When implanted with proximal surface 202'''' of fusion spacer 200'''' positioned against resected surface 34 of tibia 12 (FIG. 5B), stem 220'''' may extend beyond resected surface 34 and into the space once occupied by post 31 of the prosthetic tibial component 30 (FIG. 4).

b. Subtalar Joint

Figure 6:
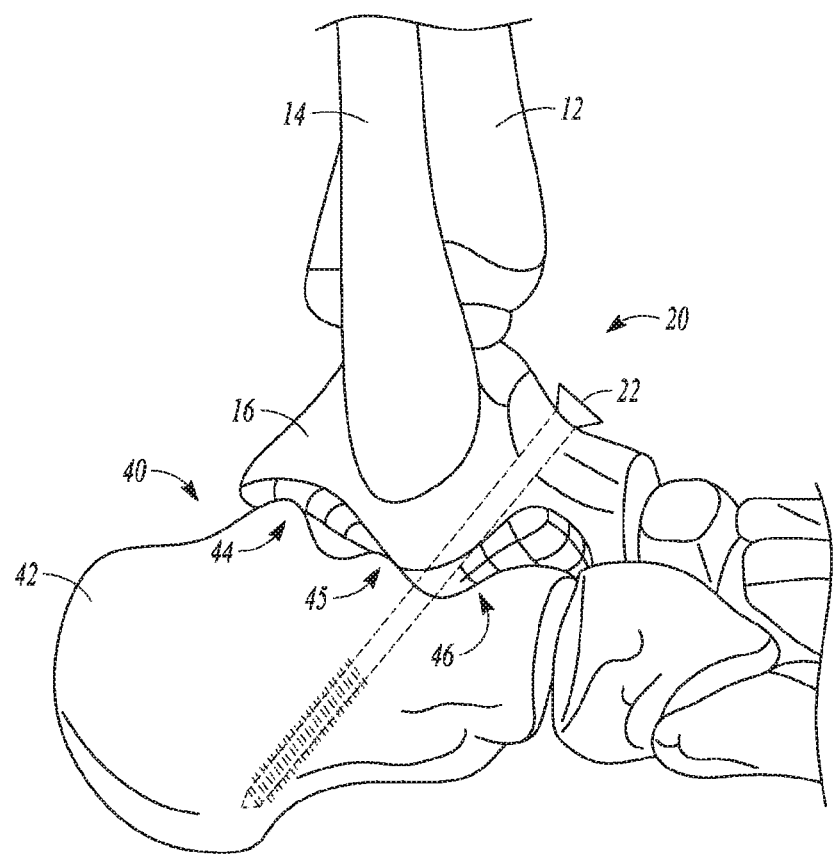
FIG. 6 is a lateral elevational view of a patient's subtalar joint with screws implanted therein to fuse the subtalar joint.

Referring next to FIG. 6, a patient's subtalar or talocalcaneal joint 40 is shown. Subtalar joint 40 includes talus 16 and calcaneus 42. Articulation between talus 16 and calcaneus 42 occurs in three areas: the posterior articular facet 44, the middle articular facet 45, and the anterior articular facet 46. In the posterior articular facet 44, a generally concave talus 16 articulates with a generally convex calcaneus 42. In the anterior articular facet 46, a generally convex talus 16 articulates with a generally concave calcaneus 42.

If subtalar joint 40 develops arthritis, deteriorates, suffers traumatic injury, or becomes otherwise damaged, it may be necessary to perform a joint fusion procedure to prevent further articulation of subtalar joint 40. The fused subtalar joint 40 becomes rigid and immobile, like a single bone. Traditionally, subtalar joint 40 was fused by driving one or more screws 22 through talus 16 and into calcaneus 42, as shown in FIG. 6. Screws 22 would prevent further articulation of talus 16 relative to calcaneus 42.

In FIGS. 7A-7D, a third exemplary fusion spacer 300 is provided in the form of a subtalar posterior facet spacer. Fusion spacer 300 may be constructed entirely or substantially entirety of a highly porous biomaterial 1000 in the form of a metal-coated scaffold, as described further above and as shown in FIG. 3B.

The posterior articular facet 44 of subtalar joint 40 may be prepared to receive fusion spacer 300 by resecting talus 16 along resected surface 48, which is illustratively concave, and by resecting calcaneus 42 along resected surface 49. which is illustratively convex.

Figure 7A:
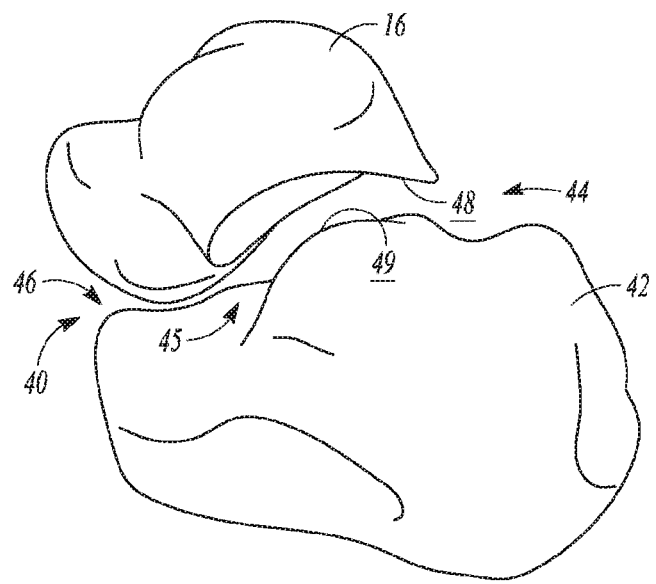
FIG. 7A is a perspective view of a patient's resected subtalar joint.
Figure 7B:
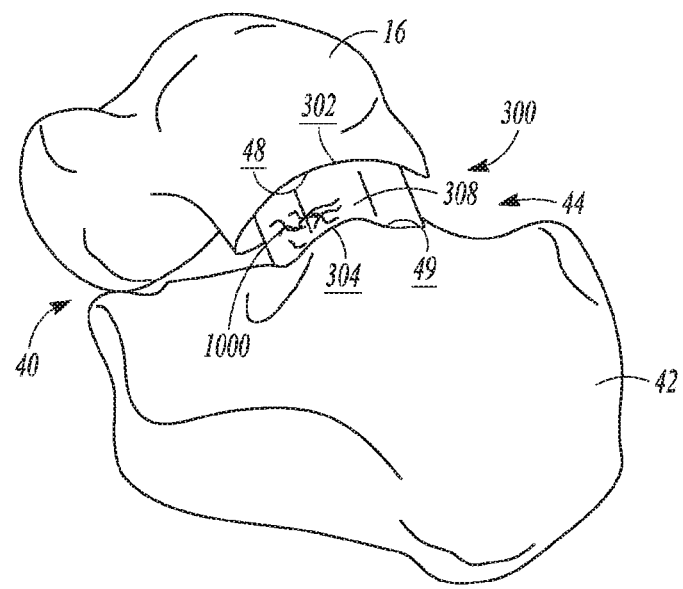
FIG. 7B is a perspective view of the resected subtalar joint of FIG. 7A with a third exemplary fusion spacer implanted therein to fuse the subtalar joint.
Figure 7C:
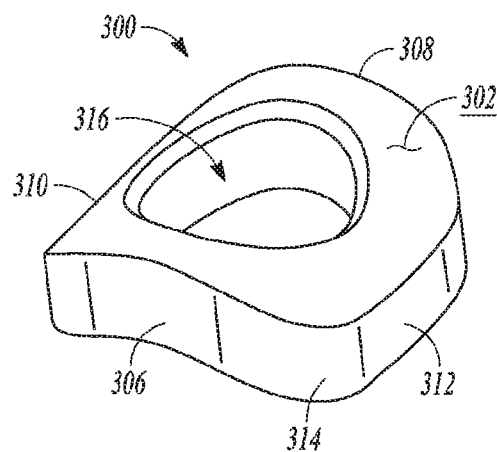
FIG. 7C is a proximal perspective view of the third fusion spacer of FIG. 7B.
Figure 7D:
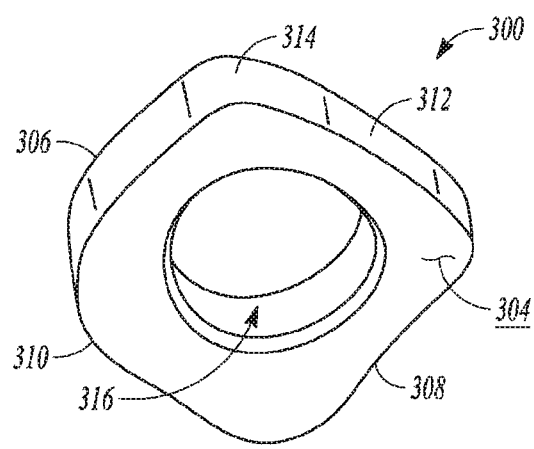
FIG. 7D is a distal perspective view of the third fusion spacer of FIG. 7B.

As shown in FIGS. 7C and 7D, fusion spacer 300 is a generally block-shaped structure having proximal surface 302 and distal surface 304. Proximal surface 302 of fusion spacer 300 is convex in shape to interact with the concave resected surface 48 of talus 16, as shown in FIG. 7B. Distal surface 304 of fusion spacer 300 is concave in shape to interact with the convex resected surface 49 of calcaneus 42, as shown in FIG. 7B. The convex proximal surface 302 may mimic the concave distal surface 304 such that fusion spacer 300 maintains a substantially constant proximal-distal thickness (i.e., the distance between proximal surface 302 and distal surface 304). Proximal surface 302 and distal surface 304 of fusion spacer 300 are illustratively square-shaped or rectangular-shaped when viewed in plan.

According to an exemplary embodiment of the present disclosure, fusion spacer 300 has a highly porous construction at least along proximal surface 302 and distal surface 304. in this manner, fusion spacer 300 may encourage bone ingrowth from talus 16 into proximal surface 302 and from calcaneus 42 into distal surface 304, thereby fusing talus 16 and calcaneus 42 via fusion spacer 300. According to another exemplary embodiment of the present disclosure, fusion spacer 300 is entirely porous in construction to encourage uninterrupted bone ingrowth from talus 16 and calcaneus 42.

Fusion spacer 300 also includes anterior wall 306, posterior wall 398, medial wall 310, and lateral wall 312 that are substantially flat and that come together at rounded or curved edges 314. As shown in FIGS. 7C and 7D, fusion spacer 300 includes a hollow interior 316 that may be configured to receive a bone graft, an osteoconductive scaffold (e.g., CopiOs® Bone Void Filler), bone cement, or a fastener, for example.

Fusion spacer 300 may be provided in various sizes to accommodate a variety of different patients. For example, fusion spacer 300 may be available in anterior-posterior depths (i.e., the distance between anterior wall 306 and posterior wall 308) of about 16 mm, about 18 mm, and about 20 mm, and medial-lateral widths (i.e., the distance between medial wall 310 and lateral wall 312) of about 16 mm, about 18 mm, and about 20 mm. Also, each fusion spacer 300 may be available in different proximal-distal thicknesses (i.e., the distance between proximal surface 392 and distal surface 394), such as about 4 mm, about 7 mm, and about 10 mm. The set may include other fusion spacers 300 in addition to those described herein.

Figure 7E:
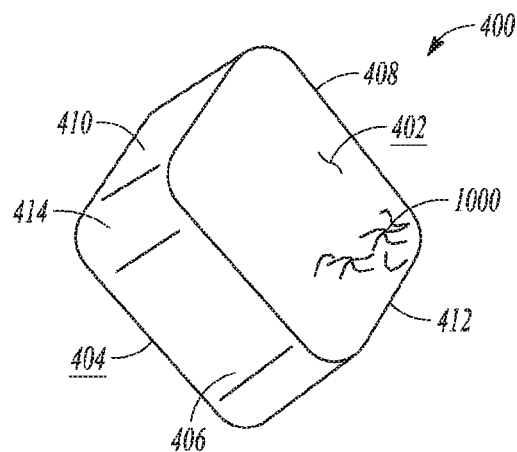
FIG. 7E is a perspective view of a fourth exemplary fusion spacer.

In FIG. 7E, a fourth exemplary fusion spacer 400 is provided in the form of a subtalar middle facet spacer. Fusion spacer 400 may be constructed entirely or substantially entirely of a highly porous biomaterial 1000 in the form of a metal-coated scaffold, as described further above and as shown in FIG. 3B.

In an exemplary embodiment, with the above-described fusion spacer 390 implanted into the posterior articular facet 44 of subtalar joint 40, fusion spacer 400 is implanted in combination therewith in the middle articular facet 45 of subtalar joint 40. It is also within the scope of the present disclosure to provide a suitably shaped fusion spacer for anterior articular facet 46 of subtalar joint 40.

Fusion spacer 400 is a generally block-shaped structure having proximal surface 402 and distal surface 404. Proximal surface 402 and distal surface 494 of fusion spacer 400 are illustratively planar, parallel surfaces and are square-shaped or rectangular-shaped when viewed in plan. Fusion spacer 400 also includes anterior wall 406, posterior wall 408, medial wall 410, and lateral wall 412 that are substantially flat and that come together at rounded or curved edges 414.

According to an exemplary embodiment of the present disclosure, fusion spacer 400 has a highly porous construction at least along proximal surface 402 and distal surface 404. In this manner, fusion spacer 400 may encourage bone ingrowth from talus 16 into proximal surface 402 and from calcaneus 42 into distal surface 404, thereby fusing talus 16 and calcaneus 42 via fusion spacer 400. According to another exemplary embodiment of the present disclosure, fusion spacer 400 is entirely porous in construction to encourage uninterrupted bone ingrowth from talus 16 and calcaneus 42.

Fusion spacer 400 may be provided in various sizes to accommodate a variety of different patients. For example, fusion spacer 400 may be available in anterior-posterior depths (i.e., the distance between anterior wall 406 and posterior wall 408) of about 8 mm, about 10 mm, and about 12 mm, and medial-lateral widths (i.e., the distance between medial wall 410 and lateral wall 412) of about 8 mm, about 10 mm, and about 12 mm. Also, each fusion spacer 400 may be available in different proximal-distal thicknesses (i.e., the distance between proximal surface 402 and distal surface 404), such as about 4 mm and about 6 mm. The set may include other fusion spacers 400 in addition to those described herein.

Figure 8A:
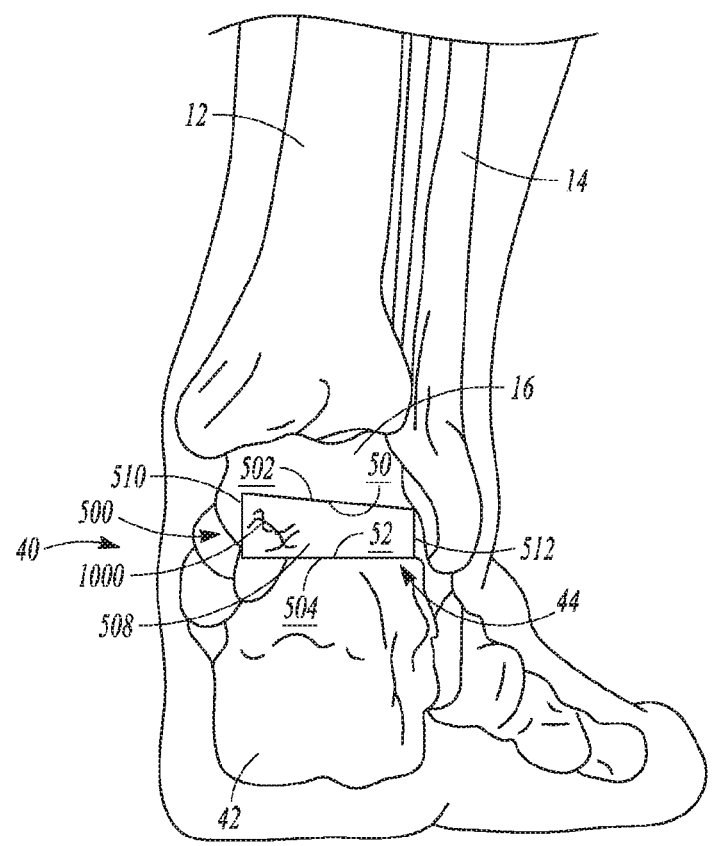
FIG. 8A is a posterior elevational view of a patient's subtalar joint with a fifth exemplary fusion spacer implanted therein to fuse the subtalar joint.
Figure 8B:
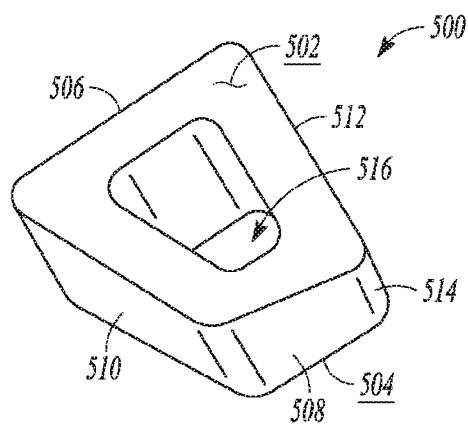
FIG. 8B is a perspective view of the fifth fusion spacer of FIG. 8A.

In FIGS. 8A-8B, a fifth exemplary fusion spacer 500 is provided in the form of a subtalar posterior facet spacer. Fusion spacer 500 may be constructed entirely or substantially entirely of a highly porous biomaterial 1000 in the form of a metal-coated scaffold, as described further above and as shown in FIG. 3B.

Unlike the above-described fusion spacer 300, which has arcuate proximal and distal surfaces 302, 304, fusion spacer 500 has generally planar proximal and distal surfaces 502, 504. Proximal and distal surfaces 502, 504 of fusion spacer 500 are illustratively trapezoidal-shaped when viewed in plan. The posterior articular facet 44 of subtalar joint 40 may be prepared to receive fusion spacer 500 by resecting talus 16 and calcaneus 42 generally planar resected surfaces 50, 52, respectively.

According to an exemplary embodiment of the present disclosure, fusion spacer 500 has a highly porous construction at least along proximal surface 502 and distal surface 504. In this manner, fusion spacer 500 may encourage bone ingrowth from talus 16 into proximal surface 502 and from calcaneus 42 into distal surface 504, thereby fusing talus 16 and calcaneus 42 via fusion spacer 500. According to another exemplary embodiment of the present disclosure, fusion spacer 500 is entirely porous in construction to encourage uninterrupted bone ingrowth from talus 16 and calcaneus 42.

Fusion spacer 500 is a generally wedge-shaped structure having anterior wall 506, posterior wall 508, medial wall 510, and lateral wall 512 that are substantially flat and that come together at rounded or curved edges 514. As shown in FIG. 8A, medial wall 510 is taller than lateral wall 512 to restore the arch and the angle of the foot. As shown in FIG. 8B, fusion spacer 500 includes a hollow interior 516 that may be configured to receive a bone graft, an osteoconductive scaffold (e.g., CopiOs® Bone Void Filler), bone cement, or a fastener, for example.

Fusion spacer 500 may be provided in various sizes to accommodate a variety of different patients. For example, fusion spacer 500 may be available in anterior-posterior depths (i.e., the distance between anterior wall 506 and posterior wall 508) of about 23 mm, about 25 mm, and about 27 mm, and medial-lateral widths (i.e., the distance between medial wall 510 and lateral wall 512) that vary from about 12 mm, about 14 mm, or about 16 mm to about 21 mm, about 23 mm, or about 25 mm. Also, each fusion spacer 400 may be available in different proximal-distal thicknesses (i.e., the distance between proximal surface 502 and distal surface 504), such as about 6 mm, about 9 mm, and about 12 mm. The set may include other fusion spacers 500 in addition to those described herein.

c. Talonavicular Joint

Figure 9A:
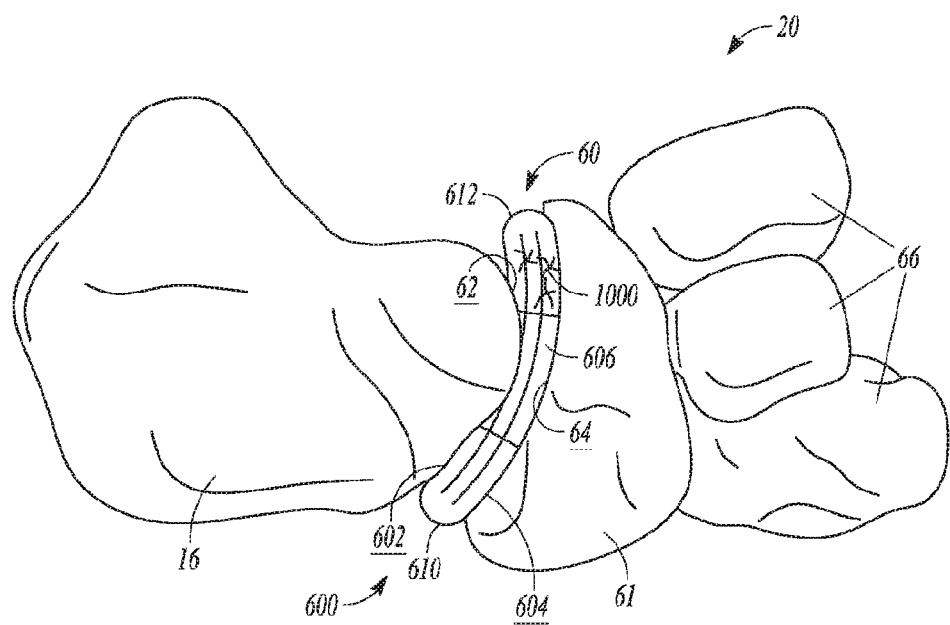
FIG. 9A is a proximal perspective view of a patient's talonavicular joint with a sixth exemplary fusion spacer implanted therein to fuse the talonavicular joint.

Referring next to FIG. 9A, a patients talonavicular joint 60 is shown. Talonavicular joint 60 includes a generally convex talus 16 and a generally concave navicular 61. Like the above-described ankle joint 10 and the above-described subtalar joint 40, talonavicular joint 60 may require fusion.

Figure 9B:
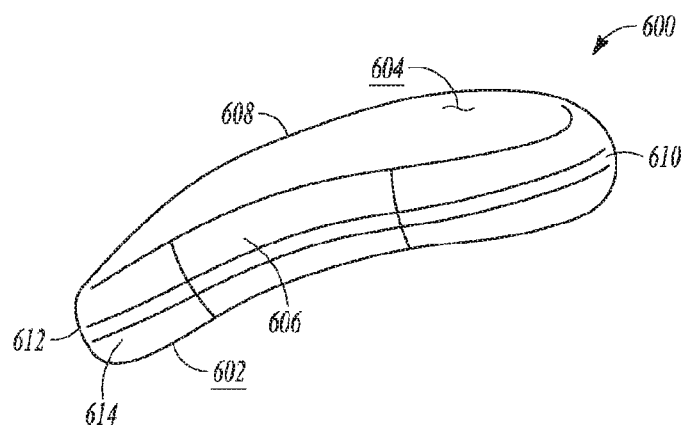
FIG. 9B is a perspective view of the sixth fusion spacer of FIG. 9A.

In FIGS. 9A-9B, a sixth exemplary fusion spacer 600 is provided to fuse talonavicular joint 60. Fusion spacer 600 may be constructed entirely or substantially entirely of a highly porous biomaterial 1000 in the form of a metal-coated scaffold, as described further above and as shown in FIG. 3B, Fusion spacer 600 is a generally chip-shaped structure having posterior surface 602 and anterior surface 604. Posterior surface 602 of fusion spacer 600 is concave in shape to interact with the generally convex resected surface 62 of talus 16, and anterior surface 604 of fusion spacer 600 is convex in shape to interact with the generally concave resected surface 64 of navicular 61, as shown in FIG. 9A. The concave posterior surface 602 may mimic the convex anterior surface 604 such that fusion spacer 600 maintains a substantially constant anterior-posterior thickness (i.e., the distance between posterior surface 602 and anterior surface 604). Posterior surface 602 and anterior surface 604 of fusion spacer 600 are illustratively oval-shaped when viewed in plan. Fusion spacer 600 also includes proximal wall 606, distal 608, medial wall 610, and lateral wall 612 that come together at rounded or curved edges 614. The anatomical identification of each wall 606, 608, 610, 612 may vary depending on how fusion spacer 600 is oriented when implanted.

According to an exemplary embodiment of the present disclosure, fusion spacer 600 has a highly porous construction at least along posterior surface 602 and anterior surface 604. In this manner, fusion spacer 600 may encourage bone ingrowth from talus 16 into posterior surface 602 and from navicular 61 into anterior surface 604, thereby fusing talus 16 and navicular 61 via fusion spacer 600. According to another exemplary embodiment of the present disclosure, fusion spacer 600 is entirely porous in construction to encourage uninterrupted bone ingrowth from talus 16 and navicular 61.

Fusion spacer 600 may be provided in various sizes to accommodate a variety of different patients. For example, fusion spacer 600 may be available in proximal-distal heights (i.e., the distance between proximal wall 606 and distal wall 608) of about 14 mm, about 18 mm, and about 22 mm, and medial-lateral widths (i.e., the distance between medial wall 610 and lateral wall 612) of about 26 mm, about 30 mm, and about 34 mm. Also, each fusion spacer 600 may be available in different anterior-posterior thicknesses (i.e., the distance between posterior surface 602 and anterior surface 604), such as about 6 mm, about 9 mm, and about 12 mm. The set may include other fusion spacers 600 in addition to those described herein.

The same or a similar fusion spacer 600 may also be configured for implantation between the patient's navicular 61 and multiple cuneiforms 66 (FIG. 9A). In this embodiment, fusion spacer 600 may encourage bone ingrowth from navicular 61 into posterior surface 602 and from cuneiforms 66 into anterior surface 604, thereby fusing navicular 61 and cuneiforms 66 via fusion spacer 600.

d. Other Foot Joints and Fusion Spacers

Figure 10A:
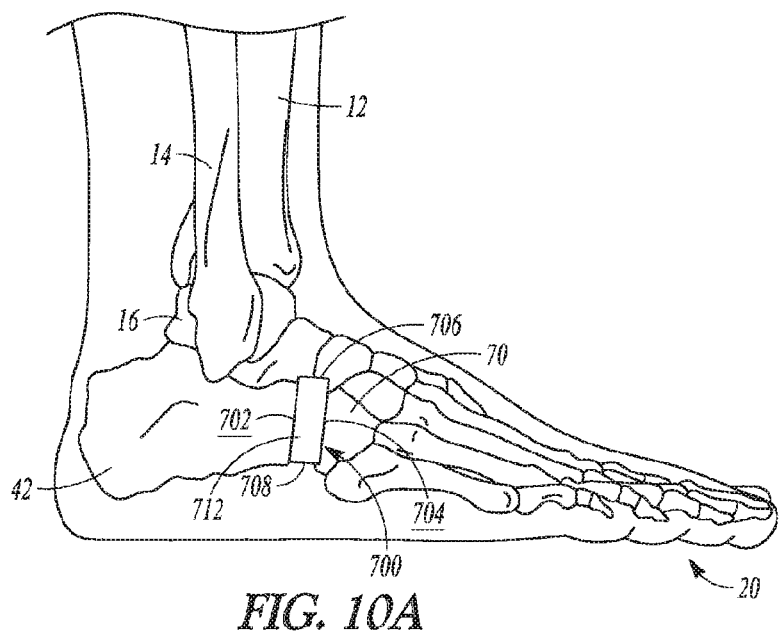
FIGS. 10A and 10B are elevational views of various joints in a patient's foot with a seventh exemplary fusion spacer implanted therein to fuse the joints.
Figure 10B:
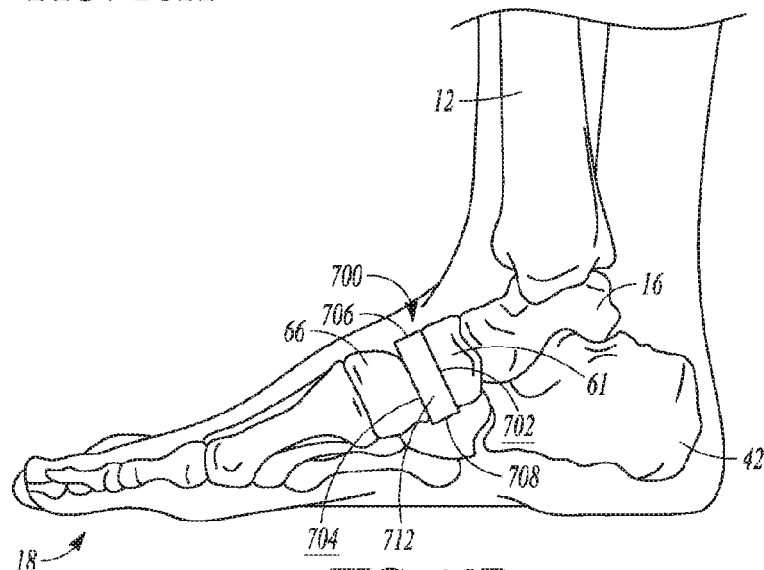
Figure 10C:
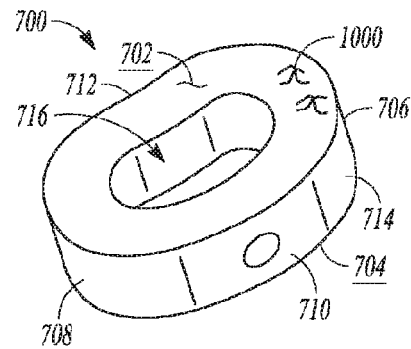
FIG. 10C is a perspective view of the seventh fusion spacer of FIGS. 10A and 10B.

A seventh exemplary fusion spacer 700 is provided in FIG. 10C. Fusion spacer 700 may be constructed entirely or substantially entirely of a highly porous biomaterial 1000 in the form of a metal-coated scaffold, as described further above and as shown in FIG. 3B.

Fusion spacer 700 is a generally kidney-shaped structure having posterior surface 702 and anterior surface 704. Posterior surface 702 and anterior surface 704 of fusion spacer 700 are illustratively planar, parallel surfaces and are kidney-shaped when viewed in plan. Fusion spacer 700 also includes proximal wall 706, distal wall 708, medial wall 710, and lateral wall 712 that come together at rounded or curved edges 714. The anatomical identification of each wall 706, 708, 710, 712 may vary depending on how fusion spacer 700 is oriented when implanted. As shown in FIG. 10C, fusion spacer 700 further includes a hollow interior 716 that may be configured to receive a bone graft, osteoconductive scaffold (e.g., CopiOs® Bone Void Filler), bone cement, or a fastener, for example.

According to an exemplary embodiment of the present disclosure, fusion spacer 700 has a highly porous construction at least along posterior surface 702 and anterior surface 704 to encourage bone ingrowth into posterior surface 702 and anterior surface 704. According to another exemplary embodiment of the present disclosure, fusion spacer 700 is entirely porous in construction to encourage uninterrupted bone ingrowth through fusion spacer 700.

Fusion spacer 700 may be provided in various sizes to accommodate a variety of different patients. Fusion spacer 100 may also be configured for implantation in a variety of different joints. In FIG. 10A, for example, fusion spacer 700 is shown implanted on lateral side 20 of the patient's foot between calcaneus 42 and cuboid 70. In FIG. 10B, fusion spacer 700 is shown implanted on medial side 18 of the patient's foot between navicular 61 and a single cuneiform

66. As an aside, the above-described fusion spacer 600 may be longer than the present fusion spacer 700 to span across multiple cuneiforms 66 (FIG. 9A).

Figure 11A:
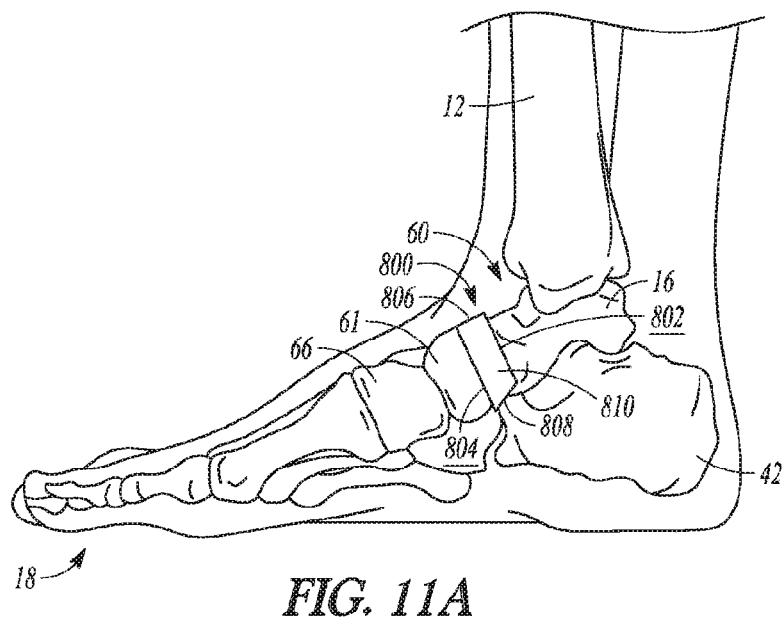
FIGS. 11A-11B are elevational views of various joints in a patient's foot with an eighth exemplary fusion spacer implanted therein to fuse the joints.
Figure 11B:
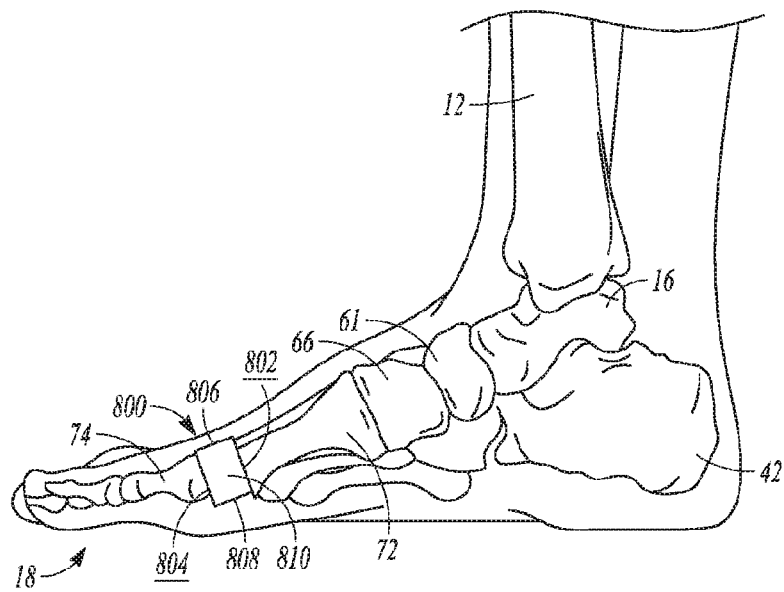
Figure 11C:
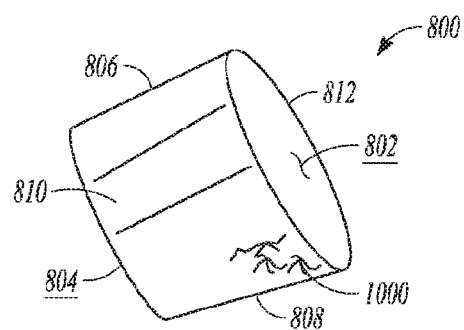
FIG. 11C is a perspective view of the eighth fusion spacer of FIGS. 11A-11B.

An eighth exemplary fusion spacer 800 is provided in FIG. 11C. Fusion spacer 800 may be constructed entirely or substantially entirely of a highly porous biomaterial 1000 in the form of a metal-coated scaffold, as described further above and as shown in FIG. 3B.

Fusion spacer 800 is a generally teardrop-shaped structure having posterior surface 802 and anterior surface 804. Posterior surface 802 and anterior surface 804 of fusion spacer 800 are illustratively planar, parallel surfaces and are teardrop-shaped when viewed in plan. Fusion spacer 800 also includes proximal wall 806, distal wall 808, medial wall 810, and lateral wall 812 that come together at rounded or curved edges 814. The anatomical identification of each wall 806, 808, 810, 812 may vary depending on how fusion spacer 800 is oriented when implanted.

According to an exemplary embodiment of the present disclosure, fusion spacer 800 has a highly porous construction at least along posterior surface 802 and anterior surface 804 to encourage bone ingrowth into posterior surface 802 and anterior surface 804. According to another exemplary embodiment of the present disclosure, fusion spacer 800 is entirely porous in construction to encourage uninterrupted bone ingrowth through fusion spacer 800.

Fusion spacer 800 may be provided in various sizes to accommodate a variety of different patients. Fusion spacer 800 may also be configured for implantation in a variety of different joints. In FIG. 11A, for example, fusion spacer 800 is shown implanted in talonavicular joint 60 on medial side 18 of the patient's foot between talus 16 and navicular 61. In FIG. 11B, fusion spacer 800 is shown implanted on medial side 18 of the patient's foot between metatarsal 72 and its corresponding phalange 74.

3. Osteotomy Spacers

In another embodiment, the fusion spacers disclosed herein may be implanted between two segments of a single bone following an osteotomy procedure, during which the bone may be cut or otherwise divided. The resection may expose the soft, inner layer of cancellous bone in each segment to receive the spacer.

Figure 12A:
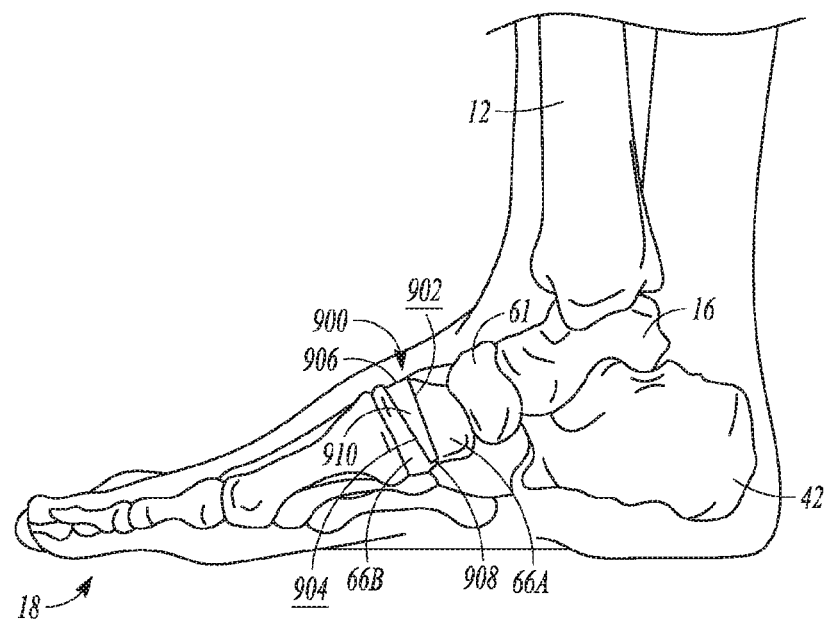
FIGS. 12A-12C are elevational views of various osteotomized bones in a patient's foot with a ninth exemplary fusion spacer implanted therein to fuse the osteotomized bones.
Figure 12B:
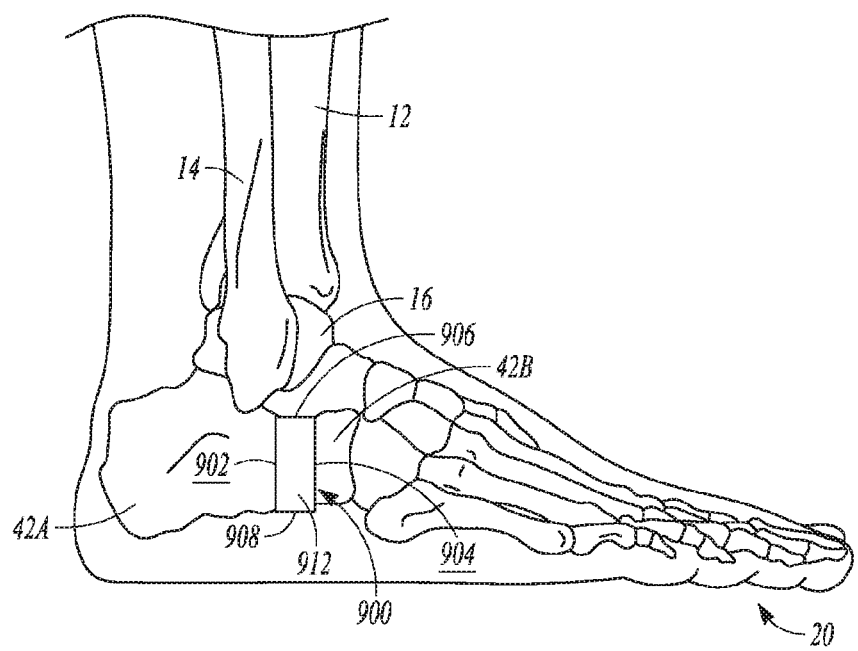
Figure 12C:
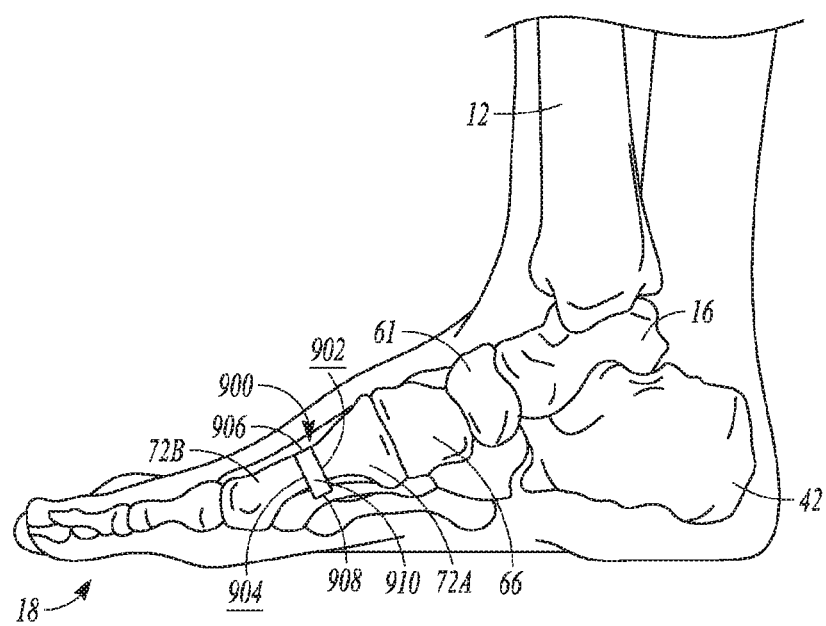
Figure 12D:
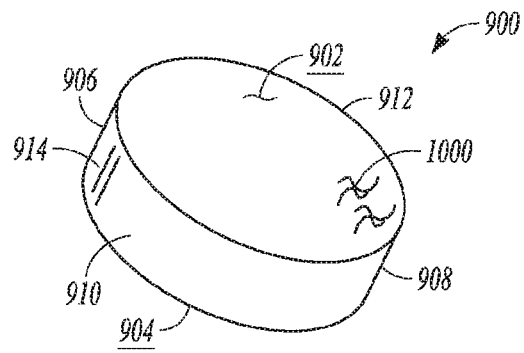
FIG. 12D is a perspective view of the ninth exemplary fusion spacer of FIGS. 12A-12C.

A ninth exemplary fusion spacer 900 is provided in FIG. 12D. Fusion spacer 900 may be constructed entirely or substantially entirely of a highly porous biomaterial 1000 in the form of a metal-coated scaffold, as described further above and as shown in FIG. 3B.

Fusion spacer 900 is a generally cylindrically-shaped or disc-shaped structure having posterior surface 902 and anterior surface 904. Posterior surface 902 and anterior surface 904 of fusion spacer 900 are illustratively planar, parallel surfaces and are circular-shaped when viewed in plan. Fusion spacer 900 also includes proximal wall 906, distal wall 908, medial wall 910, and lateral wall 912 that are curved in shape and that come together at rounded or curved edges 914. The anatomical identification of each wall 906, 908, 910, 912 may vary depending on how fusion spacer 900 is oriented when implanted.

According to an exemplary embodiment of the present disclosure, fusion spacer 900 has a highly porous construction at least along posterior surface 902 and anterior surface 904 to encourage bone ingrowth into posterior surface 902 and anterior surface 904. According to another exemplary embodiment of the present disclosure, fusion spacer 900 is entirely porous in construction to encourage uninterrupted bone ingrowth through fusion spacer 900.

Fusion spacer 900 may be provided in various sizes to accommodate a variety of different patients. For example, fusion spacer 900 may be available in proximal-distal heights (i.e., the distance between proximal wall 906 and distal wall 908) of about 12 mm, about 14 mm, about 16 mm, about 18 mm, and about 20 mm, and medial-lateral widths (i.e., the distance between medial wall 910 and lateral wall 912) of about 12 mm, about 14 mm, about 16 mm, about 18 mm, and about 20 mm. Also, each fusion spacer 900 may be available in different anterior-posterior thicknesses the distance between posterior surface 902 and anterior surface 904), such as about 5 mm and about 10 mm. The set may include other fusion spacers 900 in addition to those described herein.

Figure 12E:
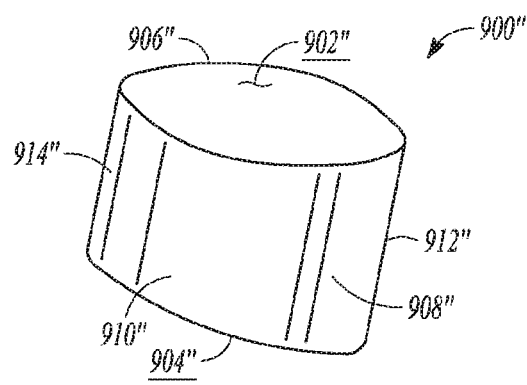
FIGS. 12E-12F are perspective views of other fusion spacers that can be used in a similar manner as the ninth fusion spacer of FIG. 12D.
Figure 12F:
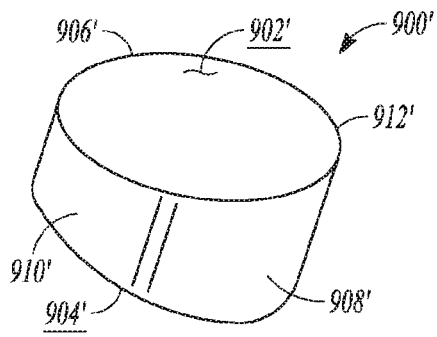

In FIG. 12F, another fusion spacer 900' is provided that is similar to the above-described fusion spacer 900, with like reference numbers indicating like elements, except as described below. Fusion spacer 900' is an angled or wedged-shaped component, with posterior surface 902' of fusion spacer 900' being angled relative to anterior surface 904' of fusion spacer 900'. For example, posterior surface 902' may be angled relative to anterior surface 904' by about 5 degrees, about 10 degrees, about 15 degrees, or about 20 degrees. In this embodiment, the anterior-posterior thicknesses of fusion spacer 900' varies, such as from about 3 mm, about 4 mm, or about 5 mm to about 6 mm, about 7 mm, or about 9 mm, for example.

In FIG. 12E, another fusion spacer 900" is provided that is similar to the above-described fusion spacers 900, 900', with like reference numbers indicating like elements, except as described below. Like fusion spacer 900' of FIG. 12F, fusion spacer 900" is also an angled or wedged-shaped component, with posterior surface 902" of fusion spacer 900" being angled relative to anterior surface 904" of fusion spacer 900", Rather than being generally cylindrical in shape, like fusion spacers 900, 900', fusion spacer 900" is more rectangular-shaped or block-shaped and includes substantially flat walls 906", 908", 910", 912" that come together at rounded or curved edges 914".

Fusion spacers 900, 900', 900", may be configured for implantation in a variety of different osteotomized bones. A desired fusion spacer 900, 900', 900", may be selected to restore the osteotomized bone to its natural, healthy shape. As shown in FIG. 12A, for example, a suitable fusion spacer 900, 900', 900", may be implanted on medial side 18 of the patient's foot between osteotomized cuneiform segments 66a, 66b (i.e. a Cotton osteotomy). As shown in FIG. 12B, a suitable fusion spacer 900, 900', 900", may be implanted on lateral side 20 of the patients foot between osteotomized calcaneus segments 42a, 42b (i.e. an Evans osteotomy). As shown in FIG. 12C, a suitable fusion spacer 900, 900', 900", may be implanted on medial side 18 of the patient's foot between osteotomized metatarsal segments 72a, 72b.

4. Ancillary Fixation

Ancillary fixation mechanisms may be used to support and stabilize the above-described fusion spacers. In one embodiment, an ancillary bone plate (e.g., a periarticular bone plate) may be implanted across the bones being fused. In the case of the fused ankle joint 10 of FIG. 3B, for example, an ancillary bone plate may be implanted across tibia 12 and talus 16 to support and stabilize fusion spacer 100 there between. In another embodiment, one or more ancillary screws may be implanted across the bones being fused. In. the case of the fused ankle joint 10 of FIG. 3B, for example, an ancillary screw may be implanted from tibia 12 (e.g., medial malleolus 13 of tibia 12) into talus 16 to support and stabilize fusion spacer 100 there between. Another ancillary screw may be implanted from fibula 14 (e.g., lateral malleolus 15 of fibula 14) into tibia 12 to further support fusion spacer 100.

5. Methods and Instruments

Figure 14:
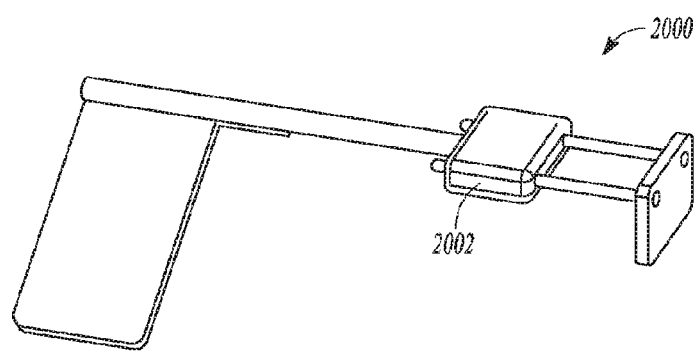
FIG. 14 is a perspective view of a cutting tool.

In operation, a surgeon prepares the bone or bones that will receive the fusion spacer. A suitable cutting tool 2000 is shown in FIG. 14. The surgeon may resect the bone(s) using tool 2000, while running a saw blade through an appropriate resection guide 2002. The surgeon may then distract the adjacent bones or bone segments to expose the area there between that will receive the fusion spacer.

Figure 13:
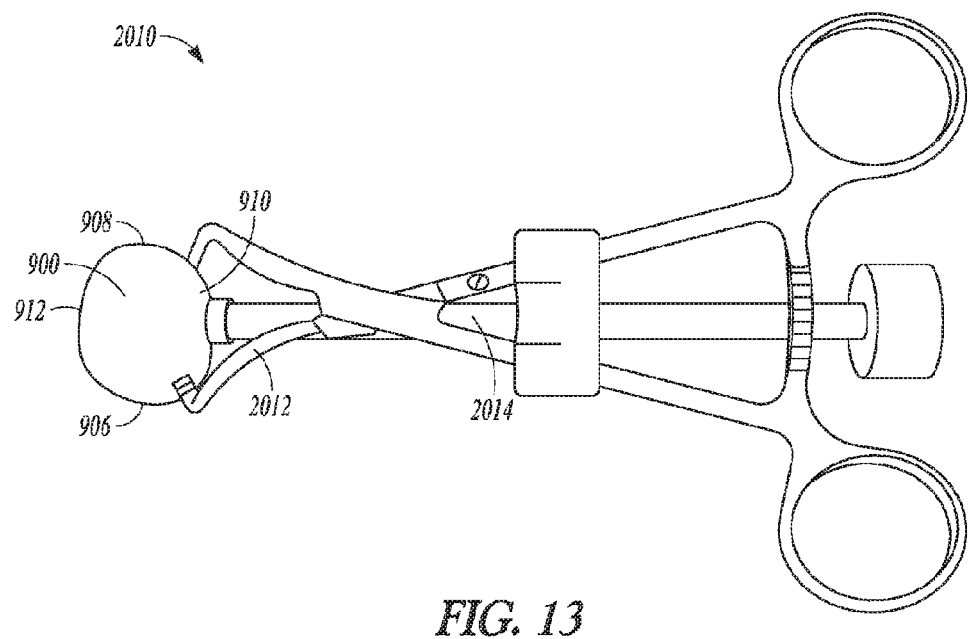
FIG. 13 is a perspective view of an insertion and extraction tool.

After preparing the bone or bones, the surgeon may insert the fusion spacer there between. A suitable insertion tool 2010 is shown in FIG. 13 with fusion spacer 900, for example. Tool 2010 includes side jaws 2012 that may be manipulated to grip the fusion spacer 900, illustratively along opposing side walls 906, 908 of fusion spacer 900. Tool 2010 also includes a central shaft 2014 that mates with or abuts the fusion spacer 900, illustratively along side wall 910 of fusion spacer 900, to apply an impaction force. Shaft 2014 may also facilitate extraction of fusion spacer 900, if necessary.

Although the following description and figures of this disclosure are directed towards an ankle fusion procedure, the present disclosure is not limited to use in the ankle The devices and methods outlined in this disclosure can be applied to any suitable joint or bone in need of resection or fusing or other modifications, The methods and devices disclosed herein for resecting bone and creating a space in a joint or in a single bone can be used in conjunction with a variety of space-filling implants and devices including fusion spacers, bone implants, artificial joint implants or other devices for repairing or altering bones.

Figure 15:
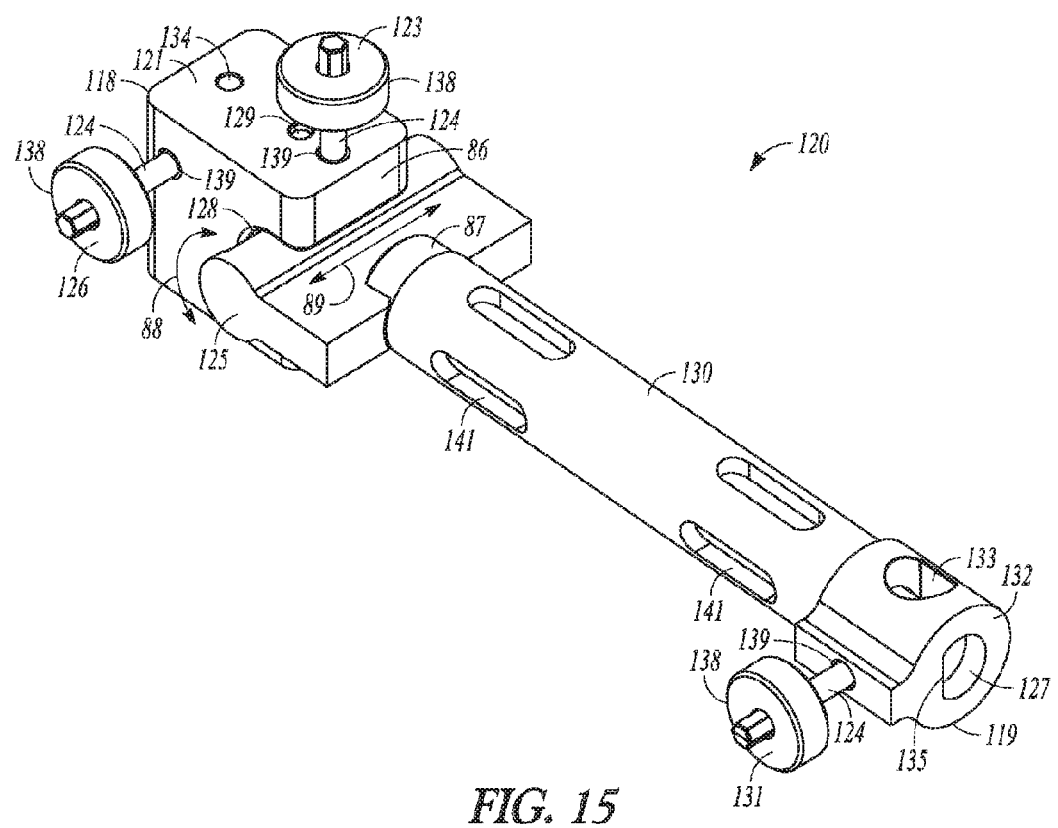
FIG. 15 is a perspective view of an anchor assembly.

An ankle resection system 250 (see FIG. 21) can include an anchor assembly 120 as illustrated in FIG. 15. Although this device will be described in relation to an ankle joint surgery, the terms "proximal", "distal", "anterior", "posterior" etc. are used for explanatory purposes only and should not be construed as limiting. At the anchor proximal end 118, the anchor assembly 120 can include an anchor main block 121 which can be block shaped, cylindrically shaped, oval shaped or otherwise and can house several apertures, openings and/or adjustment features and can include a tibia pin aperture 134 suited for pinning the anchor main block 121 to a tibia 12 (see FIG. 22). The anchor main block 121 can include a mechanism for securing the anchor main block 121 to a pin passing through the tibia pin aperture 134, such as a threaded bolt 124 tightened or loosened by a knob 138 on an anchor adjustment member 126. The threaded bolt 124 can pass through a threaded opening 139 and engage a surface of the pin passing through the tibia pin aperture 134. The tibia pin can be secured to the main block 121 in any suitable manner including using any type of holding, clamping or reversible locking mechanism. At a main block distal end 86, the anchor main block 121 can include a shaft head mating recess 128, configured to receive a shaft head 125. The shaft head 125 can be positioned on a shaft proximal end 87 of an anchor shaft member 130, which extends to a distal end 119 of the anchor assembly 120. The shaft head 125 can be configured to be adjustable in two dimensions such as an angular adjustment 88 and a medial lateral adjustment 89. The shaft head 125 can have a cylindrical shape which can allow it to be rotated within the shaft head mating recess 128 and providing the angular adjustment 88. The cylindrical shape of the shaft head 125 can also allow a medial/lateral movement within the shaft head mating recess 128 and thereby allowing both an angular adjustment 88 and a medial lateral adjustment 89 to the anchor shaft 130 which extends distally from the shaft head 125. The mating features of the shaft head 125 and the shaft head recess 128 can be reversed such that the anchor main block 121 can include a positive cylindrical member and the shaft head can include a recess to receive the positive cylindrical member.

The shaft head 125 can be locked into a position by a shaft head adjustment member 123 which can include a threaded bolt 124 attached to a knob 138. The threaded bolt 124 can pass through a threaded opening 139 and engage a surface of the shaft head 125. The anchor block 121 can include a retaining pin 129 configured to limit the medial/lateral movement of the shaft head 125 and keep the shaft head 125 from falling out of the anchor block 121 while the shaft head 125 is not locked in a position. The anchor shaft 130 can include a lumen 127 configured to receive an extension rod 140 (see FIG. 16) and allow longitudinal movement of the extension rod 140 within the length of the anchor shaft 130. The anchor shaft 130 can include sight slots 141 or openings to view a position of a rod proximal end 144 or any portion of the extension rod 140 (see FIGS. 16 and 21). The distal end 119 of the anchor assembly 120 can include a distal end attachment member 132. The distal end attachment member 132 can include a length adjustment member 131 configured to tighten or loosen a knob 138 attached to a threaded bolt 124 which can pass through a threaded opening 139, engage the extension rod 140 and lock or unlock its position. The distal end attachment member 132 can include a distal end flat 135 which can ensure that the extension rod 140 cannot rotate within the lumen 127 and can be assembled facing one direction. The distal end attachment member 132 can include an anchor frame post aperture 133 which can be configured substantially transverse to the direction of the lumen 127. In an alternative embodiment, the anchor frame post aperture 133 can be configured to engage a frame post 160 (see FIG. 21) and bypass any need for the extension rod 140 (see FIG. 16).

Figure 16:
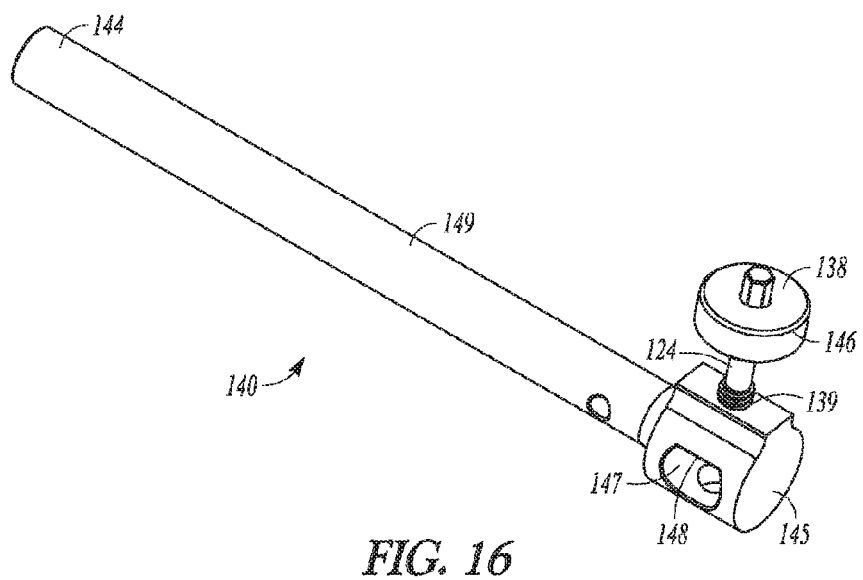
FIG. 16 is a perspective view of an extension rod.

FIG. 16 illustrates the extension rod 140 which can include a longitudinal member 149 extending from the rod proximal end 144 to a rod distal end 145. The extension rod 140 can be shaped in cross section as round, square, oval or otherwise and can include at least one flat 143 (see FIG. 21) along at least a portion of its length, configured to mate with a distal end flat 135 of the anchor shaft 130 (see FIG. 15) and which can ensure that the extension rod 140 can be positioned in the lumen 127 of the anchor assembly 120 in only one orientation. The rod distal end 145 can include a frame post aperture 147 configured to receive a frame post 160 (see FIG. 21). The frame post aperture 147 can include a geometry such as a frame post aperture flat 148 configured to mate with a frame post flat 161 and limit the orientation of the connection between the extension rod 140 and the frame 150. The geometry of the mating features of the extension rod 140, such as flat 143 and distal end member 132, such as distal end flat 135, can include any type of polygon, key/keyway, star shape, positive/negative feature which can limit orientation to one direction (see FIGS. 15, and 21). Similar geometries can be applied to the mating features of the anchor frame post aperture 133 or the frame post aperture 147 (see FIGS. 15, 16, and 17). A proximity adjustment member 146 can provide adjustment of the position of the rod distal end 145 relative to the frame post 160 (see FIG. 22) and can include a threaded bolt 124 and a knob 138. The threaded bolt 124 can pass through a threaded opening 139, engage a surface of the frame post 160 and lock movement of the frame post 160 relative to the proximity adjustment member 146.

Figure 17:
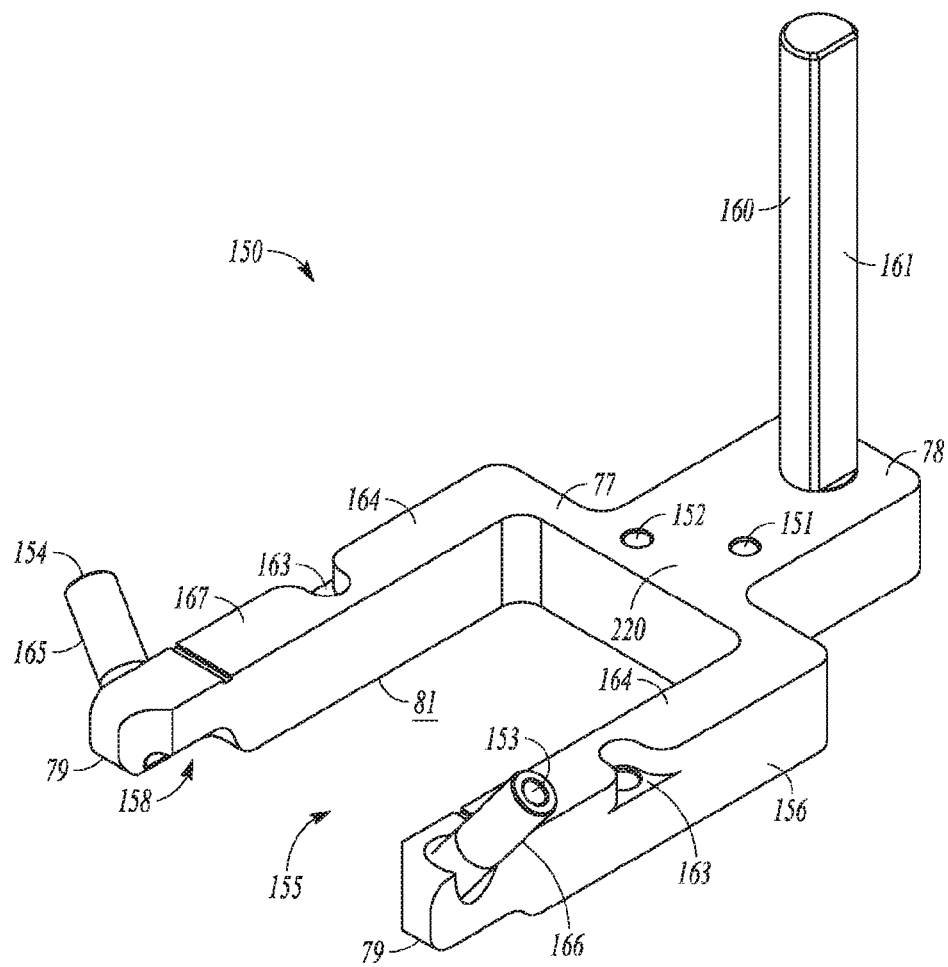
FIG. 17 is a perspective view of a resection frame.

FIG. 17 illustrates a resection frame 150 which can include a longitudinal body member 77 extending from a proximal end 78 to a distal end 79. The resection frame 150 can include a frame post 160 extending in a substantially transverse direction from the longitudinal body member 77. The longitudinal body member 77 can include a proximal body portion 220. The proximal body portion 220 can be a central area from which extend a medial leg 153 and a lateral leg 157. The longitudinal body member 77 can include an opening 155 bordered on each side by the lateral leg 157 and the medial leg 156. The opening can be configured to receive a portion of a resection guide 170 (see FIG. 21). The longitudinal body member can include an anterior face 164 opposite a posterior face 81 (not pictured). The posterior face 81 can be configured to rest against a bone or joint such as an ankle joint 10 during a resectioning procedure (see FIG. 22). The longitudinal body member 77 can include one or more apertures near the proximal end 78 such as a proximal tibial aperture 151 and a distal tibial aperture 152. These tibial apertures 151, 152 can allow pins to pass through the apertures and into a bone such as the tibia 12 (see FIG. 22) at angles configured to provide security as well as limiting any conflict with resectioning cuts. The longitudinal body member 77 can include one or more apertures near the distal end 79 such as a medial talar aperture 153 and a lateral talar aperture 154. These talar apertures 153 and 154 can allow pins to pass through the apertures and into a bone such as a talus 16 (see FIG. 22) at angles configured to provide security as well as limiting any conflict with resectioning cuts. The apertures 151, 152, 153, and 154 can include support members such as a lateral pin support 165 and a medial pin support 166 that can be configured to provide additional support to the resection frame 150 as the apertures receive pins which can be connected to bones. The medial leg 156 and the lateral leg 157 can include an attaching member 163 configured to provide attachment for the resection guide 170 (see FIG. 21). The attachment member 163 can include a threaded hole, a threaded stud, or a clamping mechanism. The distal end 79 can include a posterior recess 158 configured to allow clearance for a bone formation and can be a cut out shape oriented towards the posterior face 81.

A resection frame such as resection frame 150 can be shaped and configured in a variety of manners to suit a particular anatomy and to work in conjunction with a cutting guide such as guide 170, and in this regard, it will be understood that the various pieces or sections of a frame (e.g., arms, legs, etc.), whether the frame is modular or monolithic, can be provided in a variety of shapes and sizes and can be arranged in any suitable fashion so as to provide a primary opening in the frame such as opening 155 through which a bone cutting element can pass. In one example, the resection frame 150 can be configured for an ankle joint resection. In an example, a resection frame can be configured for a resection of a first metatarsophalangeal joint or an osteotomy of bones in the hand.

Figure 18:
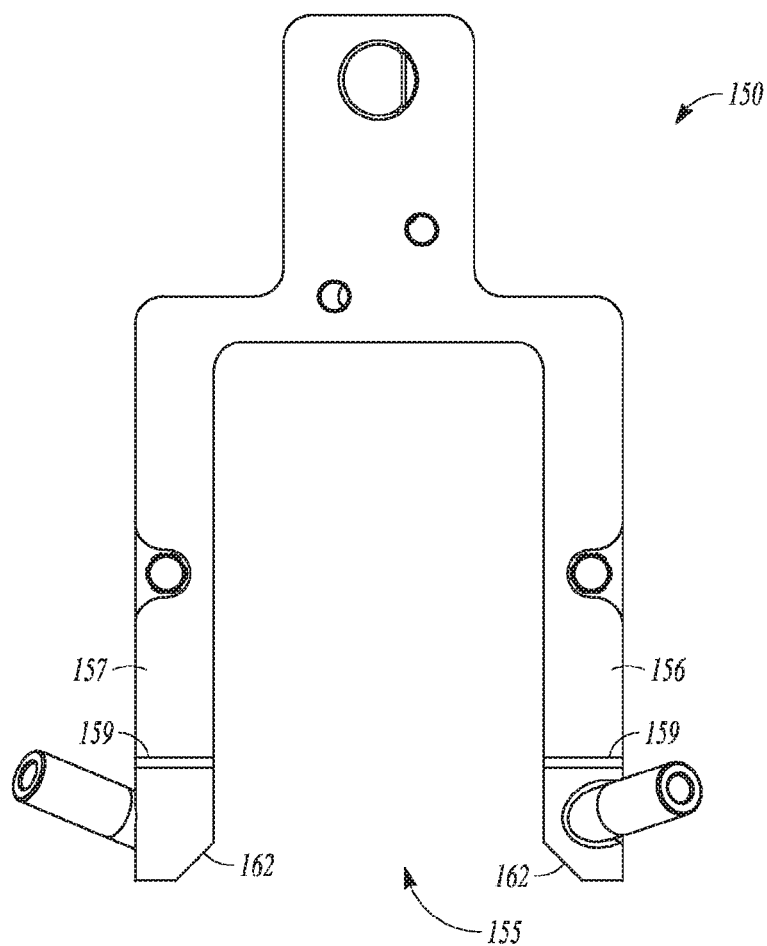
FIG. 18 is a top view of a resection frame.

FIG. 18 illustrates a top view of the resection frame 150 which can include window recesses 162. The window recesses 162 can be oriented towards the opening 155 and can provide clearance for a bone formation and allow the resection frame 150 to be positioned in a more distal direction. A scribe line 159 can be engraved or marked across a medial leg 156 and a lateral leg 157 and can be configured to aid the surgeon in placement of the resection frame 150 by orienting the scribe line 159 with a possible resection cut.

Figure 19:
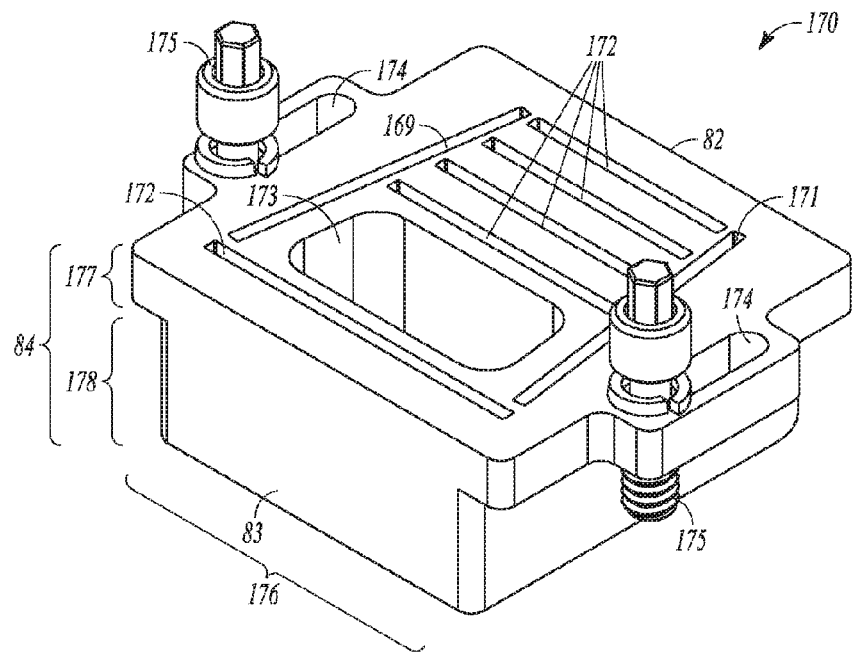
FIG. 19 is a perspective view of a resection guide.

FIG. 19 illustrates a resection guide 170. The resection guide 170 can provide slots, openings or other interior or exterior surfaces which act as directional guides and supports for a bone cutting element 190 (see FIG. 22). A resection guide such as resection guide 170 and any associated bone cutting element-guiding surfaces can be shaped and configured in any suitable manner to fit a particular anatomy and to work in conjunction with a resection frame such as resection frame 150. The resection guide 170 can have its associated slots or openings shaped to provide cuts for any form or location of resection. In one example, the resection guide 170 can be configured for an ankle joint resection. In another example, the resection guide 170 can be configured for a resection of a first metatarsophalangeal joint or an osteotomy of bones in the hand. In an example the resection guide 170 could provide slots shaped to receive a bone saw or bone knife, In another example the resection guide 170 could have drill guides or a combination of saw guides and drill guides. The resection guide 170 can be rectangular, round, oval, or oblong and can have a guide proximal end 82 and a guide distal end 83. The guide body 84 can be divided into an anterior body 177 and a posterior body 178. The posterior body 178 can be shaped with a width 176 small enough to be received in the opening 155 of the resection frame 150 (see FIGS. 18 and 21). The anterior body 177 can be configured to be wide enough to engage the anterior face 164 of the resection frame 150, such that the frame can provide support for the resection guide 170. The resection guide 150 can be configured without an anterior body portion 178 and have the guide body 84 anterior to the anterior face 104 of the resection frame 150 (see FIGS. 18 and 21).

Figure 20:
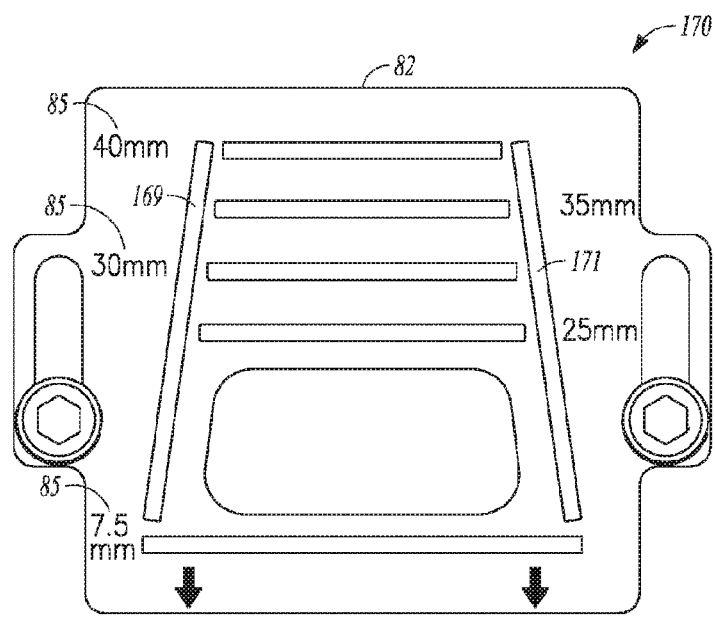
FIG. 20 is a top view of a resection guide.
Figure 21:
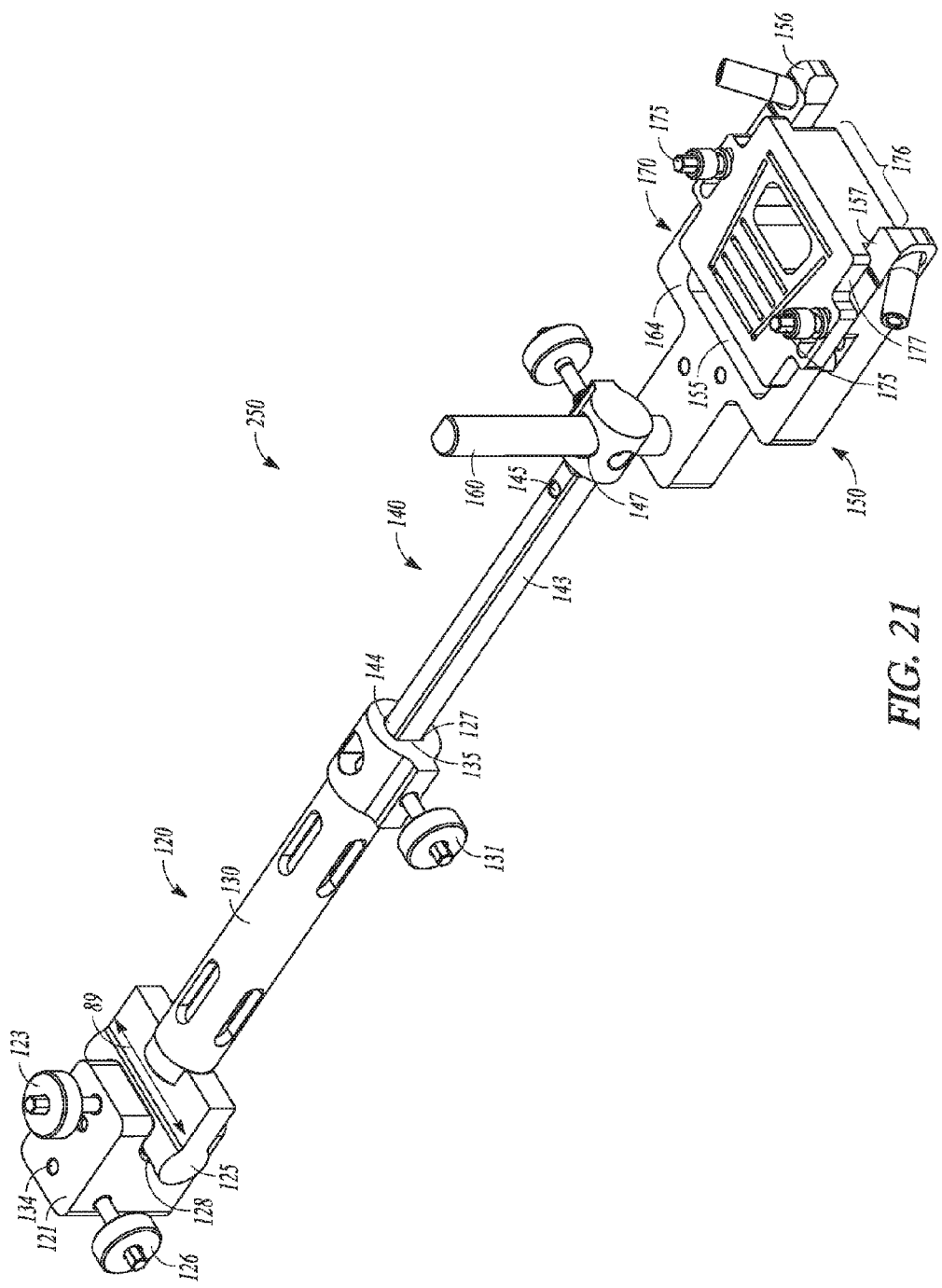
FIG. 21 is a perspective view of an ankle joint resection system.
Figure 22:
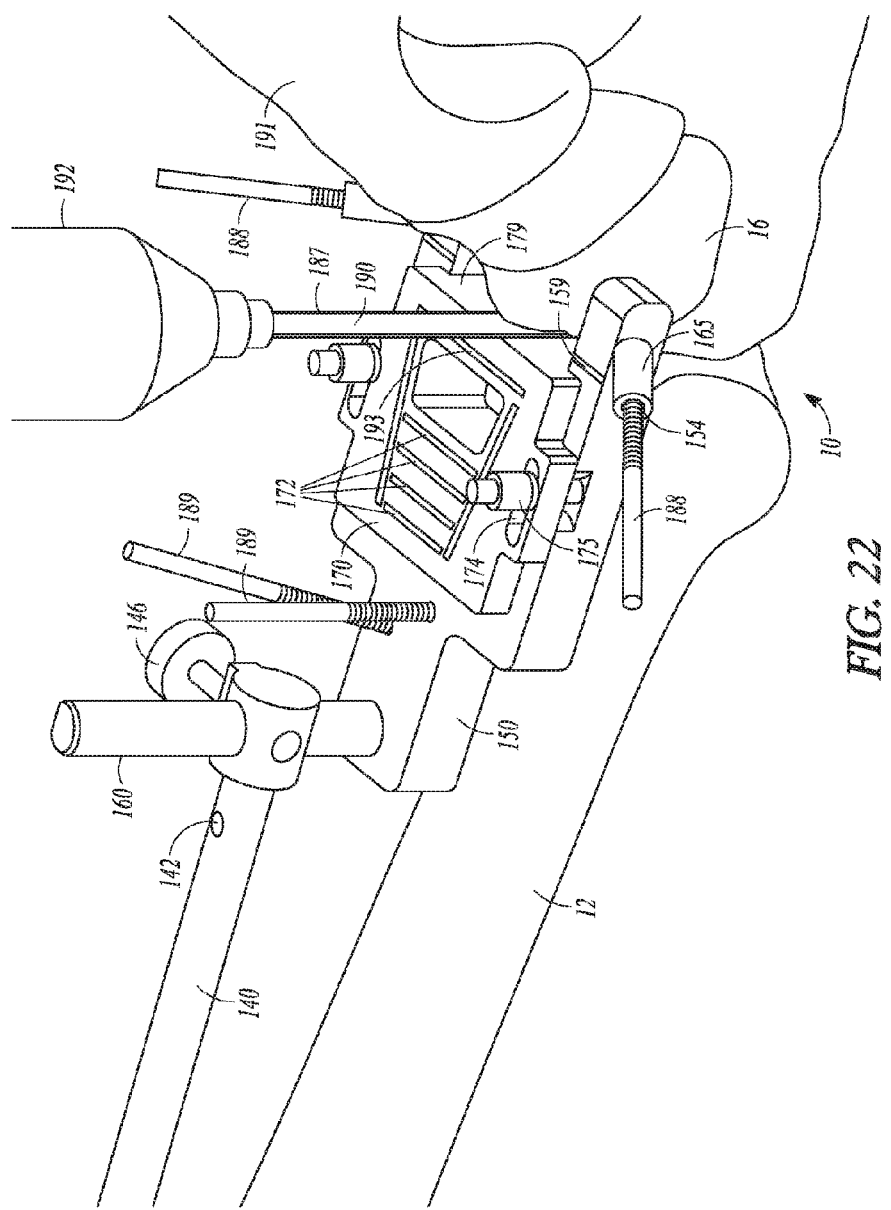
FIG. 22 is a perspective view of a talus cut.

The guide distal end 83 can have a surface such as a distal aspect 179 that can be shaped to act as a guide for a bone cutting element 190 (see FIG. 22). The distal aspect can be planar to allow a bone cutting element 190 such as a saw blade or a knife blade to engage and be guided by the distal aspect 179 during a bone cutting procedure. The guide body 84 can include a series of transverse cutting slots 172 which can allow the surgeon to select a size of a resected bone void 182 (see FIG. 27) bordered on a distal end by the cut aided by the distal aspect 179 and bordered on a proximal end by a cut aided by the selected transverse cutting slot 172. The resection guide 170 can include a lateral cutting slot 169 and a medial cutting slot 171. The lateral cutting slot 169 and the medial cutting slot 171 can connect cuts made using the distal aspect 179 and the transverse cutting slot 172. In an example, the cutting slots 169 and 171 and a transverse cutting slot 172 can be connected and need not be straight as shown. The resection guide 170 can include a cut out 173 which can aid the surgeon in viewing anatomical features the resection guide 170 is positioned over. The anterior body 177 can include proximal/distal adjustment slots 174 which can allow the resection guide 170 to be moved relative to the resection frame 150 (see FIG. 22). Bolts 175 can be used to lock any movement between the resection guide 170 and the resection frame 150. FIG. 20 illustrates a top view of the resection guide 170. The lateral cutting slot 169 and the medial cutting slot 171 can be angled inwardly towards the proximal end 82 to provide resection cuts for an ankle resection system 250 (see FIG. 21). The resection guide can include slot markings 85 which can correlate to a selected fusion spacer or bone implant size. The resection guide 150 can be configured in series of sizes such as small, medium and large; to correlate to anatomical variations in body sizes.

FIG. 21 illustrates an assembled ankle resection system 250. Depending on the size of a patient, either a longer or shorter extension rod 140 can be selected. In some embodiments, no extension rod 140 is used. For example, the proximal tibial anchor 120 can couple directly to the resection frame 150. The rod proximal end 144 can be positioned in the lumen 127 of the anchor shaft 130 of the anchor assembly 120. The extension rod flat 143 and the distal end flat 135 can ensure that the extension rod 140 is oriented correctly. The frame post aperture 147 located at the rod distal end 145 of the extension rod 140 is slid over the frame post 160 of the resection frame 150. The mating of the frame post aperture flat 148 (see FIG. 16) and the frame post flat 161 (see FIG. 17) can ensure correct orientation of the resection frame 150. The resection guide 170 can be supplied in a wide variety of sizes and cutting slot configurations. A surgeon can select a resection guide 170 and install it on the resection frame 150. The resection guide 170 can be located on the anterior face 164 of the resection frame 150 and can be attached or coupled on each side by bolts 175. The attachment or coupling of the resection guide 170 to the resection frame 150 can be accomplished in any manner known to those skilled in the art to allow the resection guide 170 to be repositioned such that it does not block the opening 155. In an example, the attachment or coupling can be in the form of a hinge. In an example, the resection guide 170 can be pinned on one side of the resection frame 150 and bolted on the other side. The width 176 of the posterior body 178 (see FIG. 19) of the resection guide 170 can be configured to fit in between the medial leg 156 and the lateral leg 157 of the resection frame 150. The anterior body 177 of the resection guide 170 can be configured to be wider than the opening 155 of the resection frame 150 and the lower surface (not pictured) of the anterior body 177 can rest against the anterior face 164 of the resection frame 150. The posterior body 178 (see FIG. 19) can be very close to bones such as the talus 16 and give support to cutting elements such as a saw blade 187 (see FIG. 22).

In FIG. 21, the ankle resection system 250 can be positioned over the tibia 12 and pinned to the tibia 12. Specifically, the main block 121 of the anchor assembly 120 can be positioned over the tubercle (not pictured) of the tibia 12. Using the tibia pin aperture 134, a surgeon can pin the anchor assembly 120 to a proximal end (not pictured) of the tibia 12. When a desired axis position on the tubercle has been located, a fastener, such as a 125 mm threaded fixation pin can be inserted through the tibia pin aperture 134 into the tibial tubercle. From this position, the ankle resection system 250 can be adjusted in several ways to locate the resection guide 170 at a correct position for resectioning. In some examples a fusion spacer 100 is used with an intramedullary nail 194 and the hollow interior 116 of the fusion spacer 100 can be aligned with the intramedullary canal 195 (see FIGS. 3C and 28) of a bone. In an example of an ankle resectioning, an axial angle of the ankle resection system 250 can be changed by rotating the system 1 about the pin (not pictured) installed in the tibia pin aperture 134. Once an axis (not pictured) has been aligned with the tibia 12 (see FIG. 22), the axis adjustment member 126 can be tightened so that the anchor assembly 120 is immovable relative to a pin (not pictured) through the tibia pin aperture 134. The extension rod 140 can be slidable within the lumen 127 of the anchor shaft 124 and the position of the rod distal end 145 can be adjusted in the longitudinal direction, A slope of the ankle resection system 250 can be adjusted to match a slope of a patient's tibia by rotating the shaft head 125 within the shaft head mating recess 128. The shaft head 125 can also slide in a medial lateral adjustment 89 direction to change the position of a longitudinal axis of the extension rod 140, the anchor shaft 130, the resection frame 150 and the resection guide 170. Upon the location of a correct position, shaft head adjustment knob 123 can be tightened to restrict further movement of the shaft head 125. There are many ways that the adjustment of height, length, axial angle, vertical angle and medial/lateral movement of a resection frame 150 and a resection guide 170 can be accomplished and the examples presented here should not be construed as limiting the scope of the invention. In an example, the resection frame 150 is not attached to an anchor assembly 120 or an extension rod 140. In such an example, the unattached resection frame 150 is positioned and pinned to a joint or bone section.

FIG. 22 illustrates a resection frame 150 pinned to the tibia 12 and the talus 16. Prior to installation of talus pins 188 and tibial pins 189, the resection guide 170 can be removed the better views of the ankle joint 10. The resection frame 150 can include the scribe line 159 which can aid in the positioning of the resection frame 150. The scribe line 159 can be used to approximate a position of a most distal resectioning cut. The distal cut can remove a portion of bone that relates to the type of fusion spacer that is being considered for use. In an example, a spacer such as the first fusion spacer 100 (see FIG. 3C) is contemplated and a 5 mm talus cut can be used. In another example a spacer such as the second fusion spacer 200 (see FIG. 5C) is contemplated and a 10 mm talus cut can be used. The scribe line 159 can be positioned accordingly, using the length adjustment member 131 at the extension rod 140 to move the resection guide 170 proximally or distally (see FIG. 21). Once such a position has been attained, the frame post 160 can be moved in the anterior/posterior direction to bring the resection frame 150 closer to the bones of the ankle joint 10. Putting the resection guide 170 close to the bones can give bone cutting elements 190 such as a saw blade 187 greater stability. The anterior/posterior movement of the resection frame 170 can be locked by tightening the proximity adjustment member 146. All of the previous adjustments can be used to properly align the ankle resection system 250 and also account for any bone deformities which may be present.

Before pins are placed in the resection frame 150, the foot 191 can be placed at an advantageous angle, such as at 90 degrees to the tibia bone 12. After positioning of the foot 191 and the ankle resection system 250, the resection frame 150 can be pinned to the ankle joint 10. The proximal aperture 151 and the distal aperture 152 can provide pathways for tibial pins 189. The apertures can provide angles for the pins which provide stability and also ensure that the pins do not interfere with any resection cuts. The resection frame 150 can be pinned to the talus 16 by applying talus pins 188 through the lateral talar aperture 153 and the medial talar aperture 154 (see FIG. 17). The lateral pin support 165 and medial pin support 166 (see FIG. 17) can be configured in any length or dimension needed to provide support for the pins 188. Both the tibial and talar pin apertures can be angled in manufacture to provide stability and holding strength. Any pin aperture can be configured with a support member such as the lateral pin support 165. Any type of fastener, screw or pin, such as an 80 mm threaded fixation pin, can be used to stabilize the resection frame 150. Pin apertures can be located at any position or in any number to secure the resection frame to a selected bone or joint. Depending on the type of incision made for the resection, some pins can be inserted percutaneously. An auxiliary pin aperture 142 located on the extension rod 140 can be utilized to pin the tibia 12 and provide more stability to the ankle resection system 250.

Figure 23:
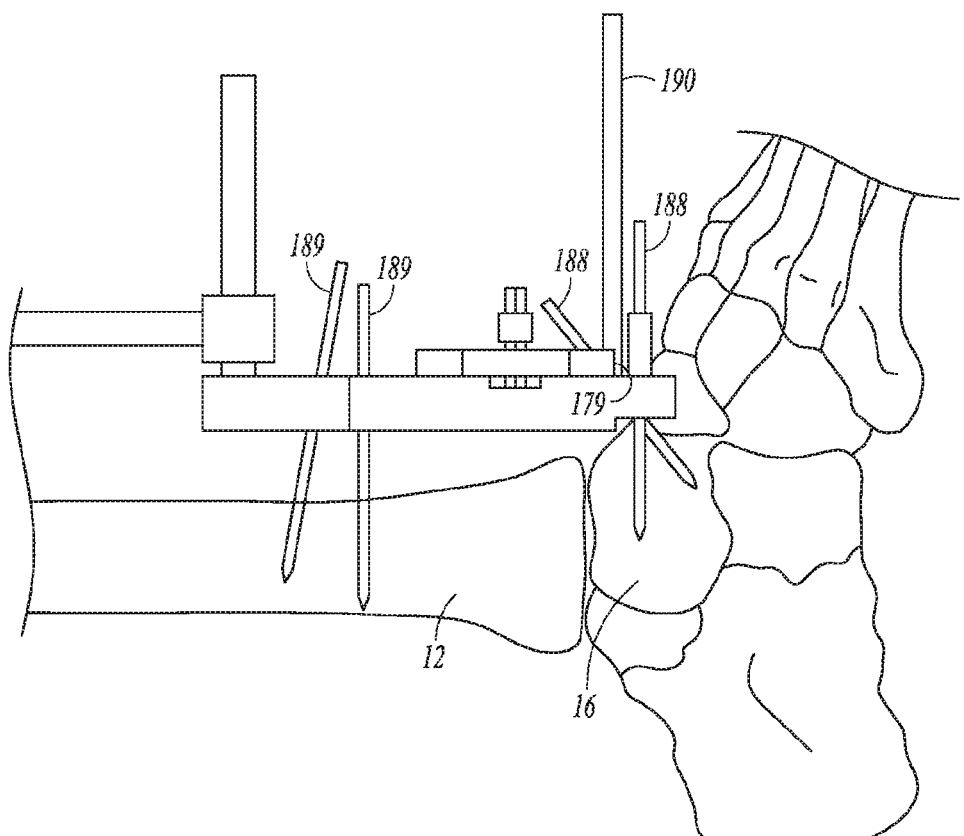
FIG. 23 is an illustration of an x-ray of pins attaching a resection frame to bones in a foot.

After pins have been placed, an additional adjustment of the resection guide 170 can be made. The resection guide 170 can be moved in the proximal/distal direction by loosening bolts 175 and allowing movement of the resection guide via the proximal/distal adjustment slot 174. Once a desired position is found, the bolts 175 can be tightened to lock the resection guide 170 to the resection frame 150. In another example to allow proximal/distal movement of the resection guide 170, the slotted feature can be located in the resection frame 150. In another example, the bolts 175 can be studs installed in the resection frame 150. The distal aspect 179 of the resection guide 170 can be used as a cutting guide for the most distal cut of the procedure, in the present example, a resection of the talus 16. Before making any bone cuts, a surgeon can x-ray the placement of the assembly as in FIG. 23. Note how the angle of the bone cutting element 190, the proximal end of the talus 16, the distal end of the tibia 12, the tibial pins 189, the talus pins 188 and the location of the distal aspect 179 can be clearly seen in the illustration of an x-ray.

Returning to FIG. 22, a cutting device 192 such as a reciprocating saw can be used with a bone cutting element 190 to resect the proximal end of the talus 16. The bone cutting element 190 can be a saw blade 187, a knife, a drill or other device. The planar face of the distal aspect 179 can act as a guide for the talus resection. After the talus resection has been made, the surface of the talus 12 can be inspected to ensure that a clean cut has been made and a good cortical rim exists which can support a fusion spacer. If necessary, the resection guide 170 can be repositioned to make a more distal cut by loosening the bolts 175 and translating the resection guide 170 distally, then re-locking the bolts 175. With the resection guide 170 still locked in place a surgeon can determine the necessary height of a tibial cut. For a fusion spacer such as the first fusion spacer 100 (see FIG. 3C), this can be a 7.5 mm slot 193. When preparing for a fusion spacer such as the second fusion spacer 200 (see FIG. 5C), a surgeon can choose to use a 25, 30, 35, or 40 mm height device and will use the corresponding transverse cutting slot 172. In another example, the resection guide 170 can be configured with a configuration of slots sized and shaped to fit any application of joint or osteotomy resectioning. A surgeon can select the appropriate spacer height by feeling through the respective transverse slots 172 with a saw blade 187 or other instrument to determine where the tibial bone 12 begins.

Figure 24:
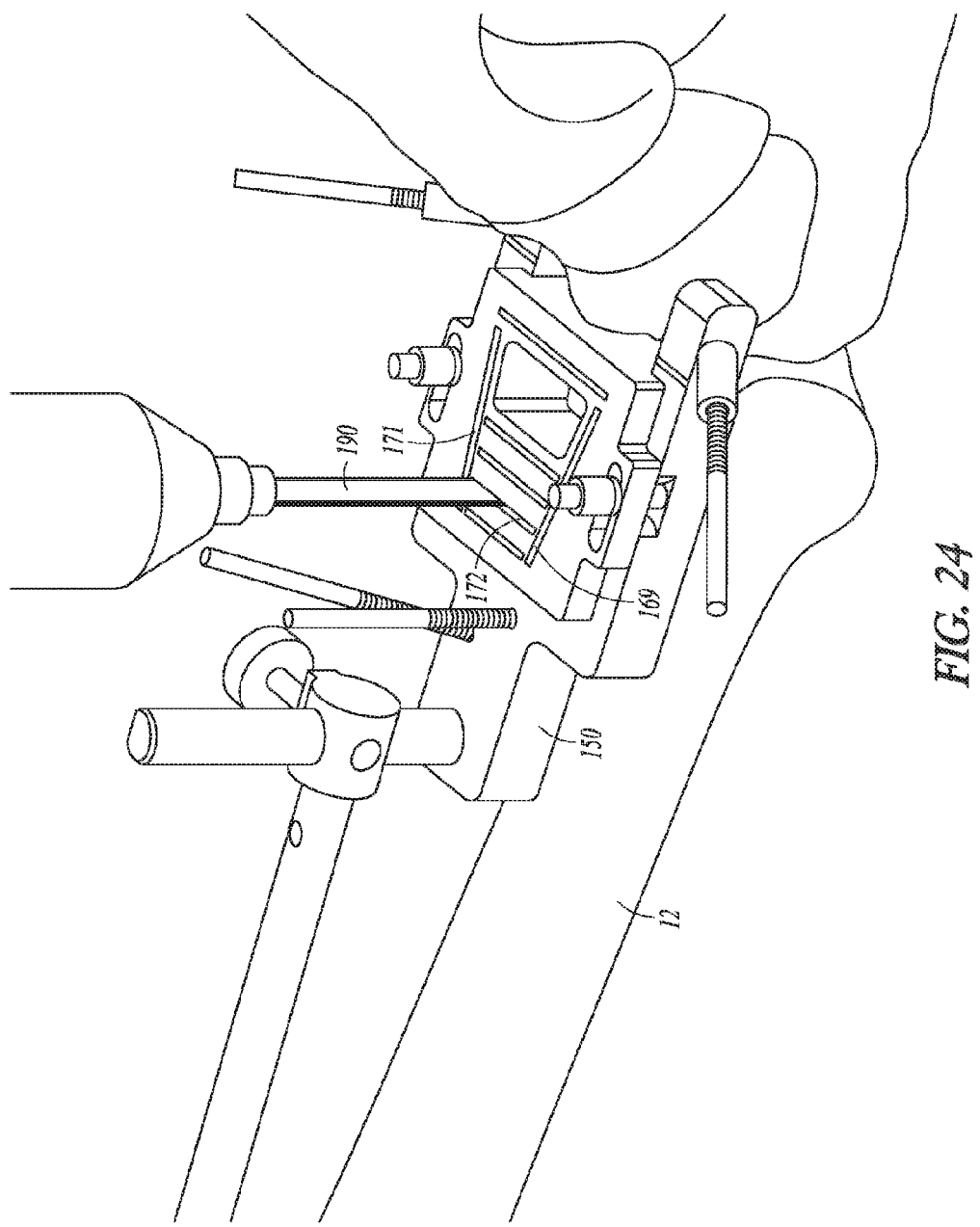
FIG. 24 is a perspective view of a tibial cut.

FIG. 24 illustrates a tibial cut being performed using one of the transverse cutting slots 172, A surgeon can use a bone cutting element 190 to cut the tibia 12 through the most distal slot on the tibial bone where a flat surface can be achieved to support a fusion spacer or bone implant. The lateral cutting slot 169 and the medial cutting slot 171 can be used to guide the bone cutting element 190 in making lateral cuts to connect the transverse cut. Bone may not be present in some surgeries on the lateral sides. After the resection has been completed, the resection guide 170 can be repositioned away from the opening 155 (see FIG. 22) of the resection frame 150 and the resection cuts can be examined to ensure that a clean surface exists to support a fusion spacer. Sharp inside corners can be adjusted with a rasp to remove any stress risers.

Figure 25:
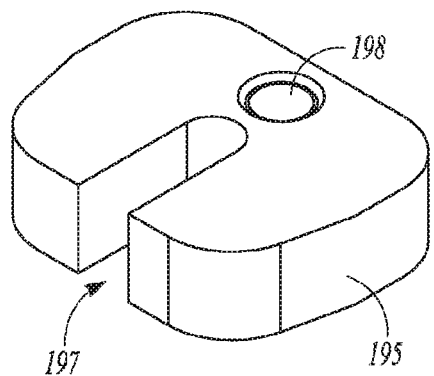
FIG. 25 is a perspective view of a provisional spacer.
Figure 26:
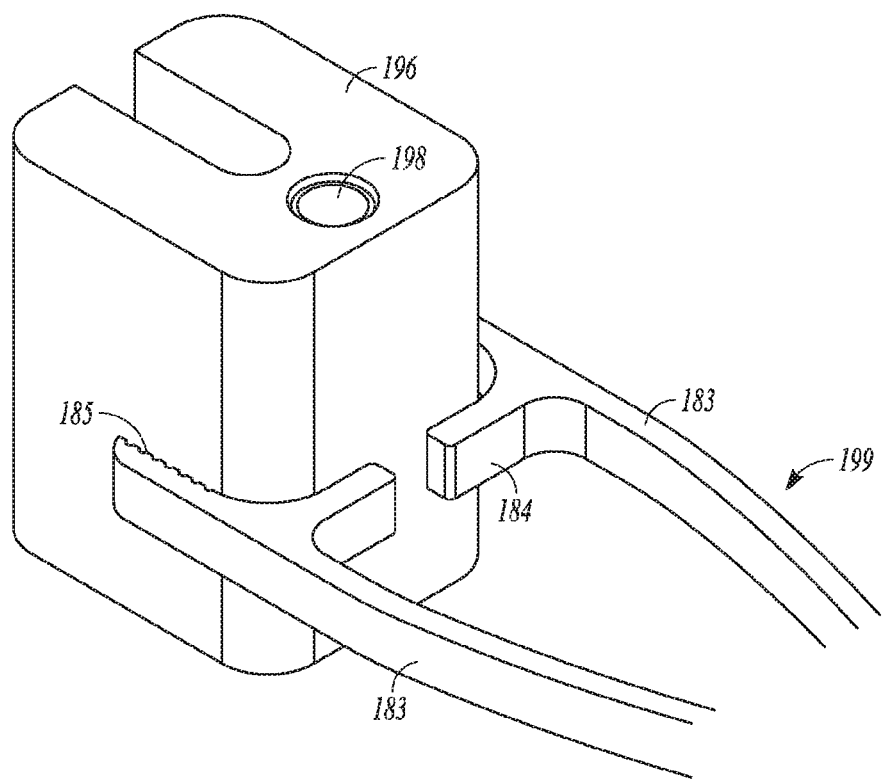
FIG. 26 is a perspective view of an insertion tool holding a provisional spacer.
Figure 27:
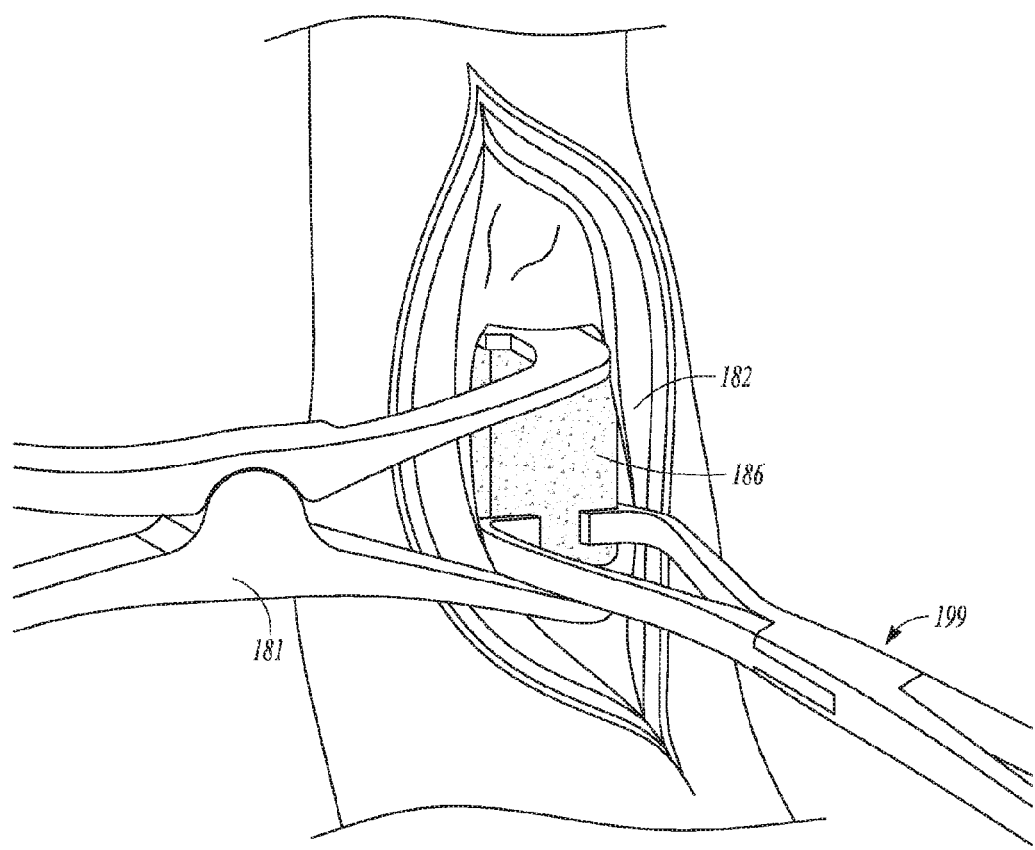
FIG. 27 is a perspective view of installation f a fusion spacer using a distractor tool and an insertion tool.

A surgeon can assess the fit of the resection surgery with the resection frame 150 pinned in place and the resection guide 170 repositioned so as not to block the opening 155 (see FIG. 18). If additional cutting is needed the resection guide 170 can be replaced and adjusted if necessary for additional cutting. A small provisional spacer 195 such as illustrated in FIG. 25 can be used for a. corresponding resection, or a large provisional spacer 196 such as illustrated in FIG. 26 such as can be used after a replacement of a total ankle replacement prosthesis as described above. The provisional spacers 195 and 196 can have a provisional slot 197 configured to provide space for a guide wire or Kirschner wire used in conjunction with a surgical procedure. Such a guide wire 117 can be seen running down the center of an intramedullary nail 194 in FIG. 28. Returning to FIGS. 25 and 26, the provisional spacers 195 and 196 can have a radiographic pin 198 which can aid in placement and location of the provisional spacer. FIG. 26 illustrates the distal end of an insertion tool 199 holding a large provisional spacer 196. The insertion tool 199 can include arms 183 of sufficient length to allow the surgeon to securely grasp the provisional spacer 196 for insertion into the resected bone void 182 (see FIG. 27). The arms 183 can include retaining members 184 which can act to orient the provisional spacer 196 and provide support for pushing the provisional spacer 196 forward. The distal end of the arms 183 can include a toothed grip 185 for increased stability. The arms 183 can be configured narrow enough while holding the provisional spacer 196, to allow a surgeon to pass the spacer or an implant through the opening 155 while the resection frame 150 (see FIGS. 24 and 18) is fixed to the talus 16 and tibia 12. In practice, a distraction tool 181 as illustrated in FIG. 27 can be used to spread the resected bone void 182 to a desired opening to insert a provisional spacer. Once the provisional spacer is in position, a surgeon can tamp the provisional with impaction tools until it is seated in its desired location. Using the distraction tool 181 and the insertion tool 199, the surgeon can then remove the provisional spacer 195 or 196. If the resection is acceptable, the surgeon can remove the resection frame 150. If more bone cutting is necessary, the surgeon can replace the resection guide 170 and adjust the location utilizing the proximal/distal adjustment slot 174 (see FIG. 24) or use a different sized or configured resection guide 170.

FIG. 27 illustrates the insertion of a large fusion spacer 186 into the resected bone void 182. The resection frame 150 (see FIGS. 24 and 18) can be removed for this procedure. In another example the resection frame 150 is kept in place for the insertion of the fusion spacer. The distraction tool 181 can be used to spread the resected bones and provide an opening to insert the large fusion spacer 186, which can be securely held by the insertion tool 199. The surgeon can tamp large fusion spacer 186 with impaction tools until it is seated in its desired location.

Figure 28:
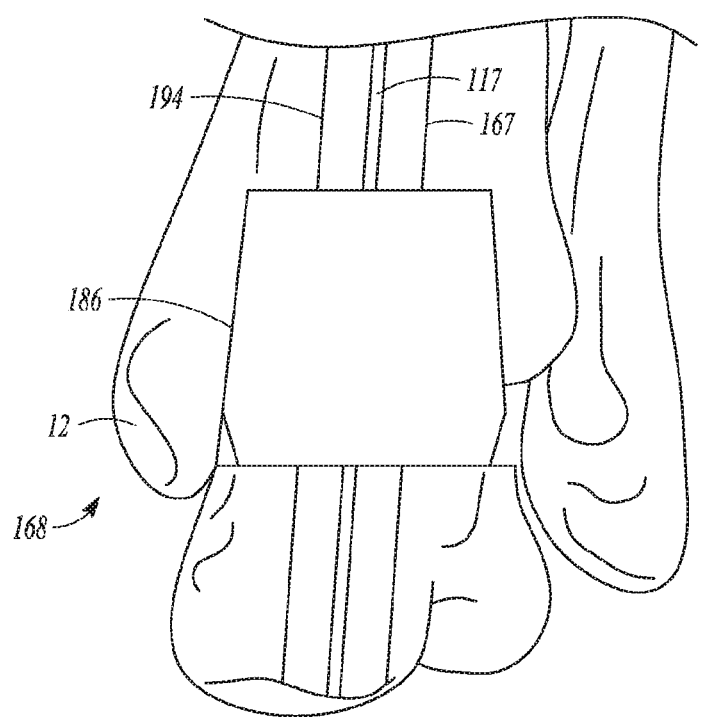
FIG. 28 is an illustration of an x-ray of an intramedullary nail and fusion spacer.

FIG. 28 illustrates an x-ray of an ankle fusion 168. Fusion spacers or bone implants can be used in conjunction with other fusion devices such as intramedullary nails, bone plates and screws. Fusion spacers can have a hollow interior 116 (see FIG. 3C) that can be sized to fit an intramedullary nail 195 such as a 10 mm nail, or a nail of any other suitable size and shape to work with a particular surgery. In an ankle joint fusion 168, after positioning the large fusion spacer 186, a surgeon can insert an intramedullary nail 195 from the bottom of the foot, through the large fusion spacer 186 and into the intramedullary canal 167 of the tibia 12. Bone plates can span a joint or an osteotomy procedure and can be attached to the bones as well as a fusion spacer. Bone screws can be placed through bones and into fusion spacers to provide stability, The above Detailed Description includes references to the accompanying drawings, which form a part of the Detailed Description. The drawings show, by way of illustration, specific embodiments in which the present ankle resection systems and methods can be practiced. These embodiments are also referred to herein as "examples." Such examples can include elements in addition to those shown or described. However, the present inventors also contemplate examples in which only those elements shown or described are provided.

The above Detailed Description is intended to be illustrative, and not restrictive. For example, the above-described examples shown or described (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for resecting bone, comprising:
   positioning a resection frame over bone, the resection frame including an opening through which a bone cutting element can pass for cutting underlying bone;
   locking a resection guide including one or more cutting slots to the resection frame to position the one or more cutting slots in a first position over the opening in the resection frame, such that the bone cutting element can pass through the one or more cutting slots; and
   passing a bone cutting element through the one or more cutting slots in the resection guide and through the opening in the resection frame to make one or more resection cuts in underlying bone that each extend in an elongate fashion along an exterior surface of the underlying bone;
   wherein the resection guide and resection frame are unlockable from one another to permit translation of one of the resection guide and the resection frame from the other of the resection guide and the resection frame in a longitudinal direction for repositioning the one or more cutting slots from the first position to a second position over the opening in the resection frame;
   wherein the resection guide is relockable to the resection frame to fix the one or more cutting slots in the second position over the opening in the resection frame.

2. The method of claim 1 further comprising anchoring the resection frame to bone.

3. The method of claim 2, wherein said coupling occurs after said anchoring.

4. The method according to any of claims 2, wherein the resection guide is decoupled from the resection frame with the resection frame remaining anchored to bone.

5. The method of claim 4, wherein the resection guide being decoupled from the resection frame uncovers the opening in the resection frame to permit a bone implant or a provisional bone implant to pass through the opening in the resection frame for placement in underlying bone.

6. The method according to any of claims 1, wherein said cut in underlying bone occurs on a first side of a joint, and wherein a further cut in underlying bone is made on a second side of the joint.

7. The method of claim 6, wherein the joint is an ankle joint.

8. The method according to any of claims 1 further comprising connecting the resection frame to a proximal tibial anchor.

9. A method for placing a bone implant or a provisional bone implant, comprising:
   anchoring a resection frame to bone, the resection frame including an opening through which the bone implant or the provisional bone implant can pass for cutting underlying bone;
   locking a resection guide to the resection frame such that the resection guide is positioned over the opening in the resection frame to block passage of the bone implant or the provisional bone implant through the opening in the resection frame while allowing passage of a bone cutting element through the resection guide and through the opening in the resection frame to cut underlying bone;
   creating a space for the bone implant or the provisional bone implant which includes passing a bone cutting element through a first cutting slot in the resection guide and through the opening in the resection frame and into underlying bone;
   unlocking the resection guide from the resection frame;
   repositioning the unlocked resection guide with respect to the opening in the resection frame such that the bone implant or the provisional bone implant can be passed through the opening in the resection frame; and
   passing the bone implant or the provisional bone implant through the opening in the resection frame and into said space.

10. The method of claim 9, wherein said positioning includes reversibly locking the resection guide to the resection frame.

11. The method of claim 10, wherein said reversibly locking occurs before said anchoring.

12. The method according to any of claims 9, wherein said repositioning includes unlocking and separating the resection guide from the resection frame.

13. The method according to any of claims 9, wherein the resection frame includes a proximal body portion with a medial leg and a lateral leg of the resection frame extending from the proximal body portion, and with the opening in the resection frame extending between said medial leg and said lateral leg.

14. The method according to any of claims 9, wherein said space is situated around an ankle joint.

* * * * *